(12) United States Patent
Baumann et al.

(10) Patent No.: US 8,703,763 B2
(45) Date of Patent: Apr. 22, 2014

(54) BRIDGED PIPERIDINE DERIVATIVES

(75) Inventors: Karlheinz Baumann, Efringen-Kirchen (DE); Luke Green, Basel (CH); Anja Limberg, Basel (CH); Thomas Luebbers, Loerrach (DE); Andrew Thomas, Binningen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 83 days.

(21) Appl. No.: 13/405,404

(22) Filed: Feb. 27, 2012

(65) Prior Publication Data

US 2012/0225884 A1    Sep. 6, 2012

(51) Int. Cl.
| A01N 43/00 | (2006.01) |
| A61K 31/55 | (2006.01) |
| C07D 413/00 | (2006.01) |
| C07D 415/00 | (2006.01) |
| C07D 417/00 | (2006.01) |
| C07D 419/00 | (2006.01) |

(52) U.S. Cl.
USPC .................................. 514/217.04; 540/598

(58) Field of Classification Search
None
See application file for complete search history.

(56) References Cited

FOREIGN PATENT DOCUMENTS

| WO | 01/81309 | 11/2001 |
| WO | 2009/103652 | 8/2009 |

OTHER PUBLICATIONS

Morihara et al., "Neurochem." 83:1009-1012 (2002).
Kukar et al., "Nature Med." 11:545-550 (2005).
Narlawar et al., "J. Med. Chem." 49:7588-7591 (2006).
Stock et al., "Bioorganic & Medicinal Chemistry Letters" 16(8):2219-2223 (2006).
"International Search Report—PCT/EP2012/053301 mailed Mar. 27, 2012".
Takahashi et al., "J. Biol. Chem." 278:18644-18670 (2003).
Weggen et al., "Nature" 414:212-216 (2001).
Clarke et al., "J. Biol. Chem." 281:31279-31289 (2006).
Perretto et al., "J. Med. Chem." 48:5705-5720 (2005).
Lleo et al., "Nature Med." 10:1065-1066 (2004).
Miskevich et al., "The Journal of Neuroscience" 22(1):226-238 (2002).
Nettekoven et al., "Synthesis" 11:1649-1652 (2003).

Primary Examiner — Jeffery H Murray

(57) ABSTRACT

The present invention relates to compounds of formula I

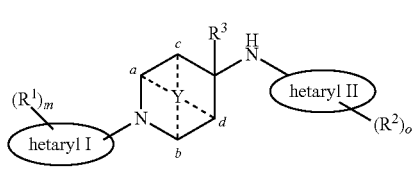

I hetaryl I, hetaryl II, $R^1$, $R^2$, $R^3$, Y, m, and o or to pharmaceutically active acid addition salts thereof. The present compounds of formula I are modulators for amyloid beta and thus, they may be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

13 Claims, No Drawings

BRIDGED PIPERIDINE DERIVATIVES

PRIORITY TO RELATED APPLICATION(S)

This application claims the benefit of European Patent Application No 11156587.5, filed Mar. 2, 2011, which is hereby incorporated by reference in its entirety.

BACKGROUND OF THE INVENTION

Alzheimer's disease (AD) is the most common cause of dementia in later life. Pathologically, AD is characterized by the deposition of amyloid in extracellular plaques and intracellular neurofibrillary tangles in the brain. The amyloid plaques are mainly composed of amyloid peptides (Aβ peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Aβ peptides are derived from the same domain of the APP.

Aβ peptides are produced from APP through the sequential action of two proteolytic enzymes termed β- and γ-secretase. β-Secretase cleaves first in the extracellular domain of APP just outside of the trans-membrane domain (TM) to produce a C-terminal fragment of APP containing the TM- and cytoplasmatic domain (CTFβ). CTFβ is the substrate for γ-secretase which cleaves at several adjacent positions within the TM to produce the Aβ peptides and the cytoplasmic fragment. Various proteolytic cleavages mediated by γ-secretase result in Aβ peptides of different chain length, e.g. Aβ38, Aβ40 and Aβ42. The latter one is regarded to be the more pathogenic amyloid peptide because of its strong tendency to form neurotoxic aggregates.

The β-secretase is a typical aspartyl protease. The γ-secretase is a proteolytic activity consisting of several proteins, its exact composition is incompletely understood. However, the presenilins are essential components of this activity and may represent a new group of atypical aspartyl proteases which cleave within the TM of their substrates and which are themselves polytopic membrane proteins. Other essential components of γ-secretase may be nicastrin and the products of the aph1 and pen-2 genes. Proven substrates for γ-secretase are the APP and the proteins of the Notch receptor family, however, γ-secretase has loose substrate specificity and may cleave further membrane proteins unrelated to APP and Notch.

The γ-secretase activity is absolutely required for the production of Aβ peptides. This has been shown both by genetic means, i.e., ablation of the presenilin genes and by low-molecular-weight inhibitory compounds. Since according to the amyloid hypothesis for AD the production and deposition of Aβ is the ultimate cause for the disease, it is thought that selective and potent inhibitors of γ-secretase will be useful for the prevention and treatment of AD.

An alternative mode of treatment is the modulation of the γ-secretase activity which results in a selective reduction of the Aβ42 production. This will result in an increase of shorter Aβ isoforms, such as Aβ38, Aβ37 or others, which have reduced capability for aggregation and plaque formation, and are less neurotoxic. Compounds which show this effect on modulating γ-secretase activity include certain non-steroidal anti-inflammatory drugs (NSAIDs) and related analogues (Weggen et al. Nature, 414 (2001) 212-16).

Numerous documents describe the current knowledge on γ-secretase modulation, for example the following publications:

Morihara et al, J. Neurochem., 83 (2002) 1009-12
Jantzen et al, J. Neuroscience, 22 (2002) 226-54
Takahashi et al, J. Biol. Chem., 278 (2003) 18644-70
Beher et al, J. Biol. Chem. 279 (2004) 43419-26
Lleo et al, Nature Med. 10 (2004) 1065-6
Kukar et al, Nature Med. 11 (2005) 545-50
Perretto et al, J. Med. Chem. 48 (2005) 5705-20
Clarke et al, J. Biol. Chem. 281 (2006) 31279-89
Stock et al, Bioorg. Med. Chem. Lett. 16 (2006) 2219-2223
Narlawar et al, J. Med. Chem. 49 (2006) 7588-91

SUMMARY OF THE INVENTION

The present invention provides compounds of formula I

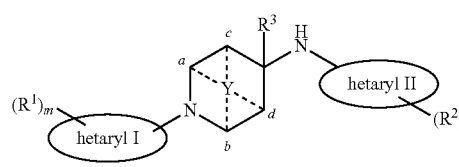

hetaryl I is a five or six membered heteroaryl group, containing 1 to 3 heteroatoms, selected from S and N;
hetaryl II is a six membered heteroaryl group, containing 1 to 3 heteroatoms, selected from S and N, or is a two membered ring system containing 1 to 4 heteroatoms selected from S and N, wherein at least one ring is aromatic in nature;
$R^1$ is lower alkyl, lower alkoxy, lower alkyl substituted by halogen or halogen;
$R^2$ is lower alkyl, lower alkyl substituted by halogen, halogen, lower alkoxy, cycloalkyl substituted by lower alkyl or lower alkyl substituted by halogen, lower alkyl substituted by hydroxy, furyl, O-benzyl, or —$(CH_2)_p$-phenyl which is optionally substituted by halogen, lower alkoxy, lower alkyl substituted by halogen, lower alkyl or cyano;
$R^3$ is hydrogen or lower alkyl;
Y is —$(CH_2)_n$—, —$CH_2OCH_2$—, —$CH_2O$—, $CH_2S$—, or —$CH_2SCH_2$— and is bonded to two of the ring carbon atoms, wherein bonding is either to ring carbon atoms a and b or to ring carbon atoms c and d;
p is 0 or 1;
m is 0, 1 or 2; if m is 2 then each $R^1$ is the same or different;
n is 2 or 3; and
o is 0, 1 or 2, if o is 2, then each $R^2$ is the same or different;
or to pharmaceutically active acid addition salts thereof.

The present compounds of formula I are modulators for amyloid beta and thus, will be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

DETAILED DESCRIPTION OF THE INVENTION

The following definitions for compounds of formula I are used:
As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkyl substituted by halogen" denotes an alkyl group as defined above, wherein at least one hydrogen atom is replaced by halogen, for example $CF_3$, $CHF_2$, $CH_2F$, $CH_2CF_3$, $CH_2CH_2CF_3$, $CF_2CHF_2$, $CH_2CF_2CF_3$ and the like.

As used herein, the term "lower alkyl substituted by hydroxy" denotes an alkyl group as defined above, wherein at least one hydrogen atom is replaced by hydroxy, for example $CH_2OH$, $CHCH_3OH$ or $C(CH_3)_2OH$.

As used herein, the term "lower alkoxy" denotes a lower alkyl group as defined above, which is bonded via an O-atom.

The term "halogen" denotes chlorine, iodine, fluorine and bromine.

The term "a five membered heteroaryl group, containing 1 to 3 heteroatoms, selected from S and N" is selected from the group consisting of

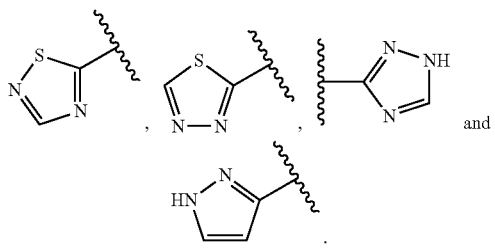

and

The preferred five membered heteroaryl group is

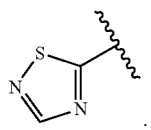

The term "a six membered heteroaryl group, containing 1 to 3 heteroatoms, selected from S and N" is selected from the group consisting of

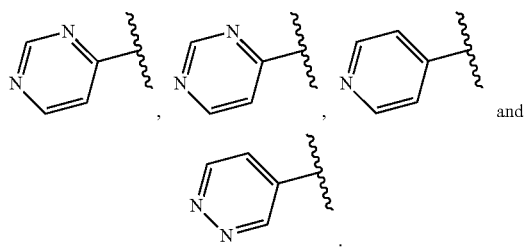

and

The preferred six membered heteroaryl groups are

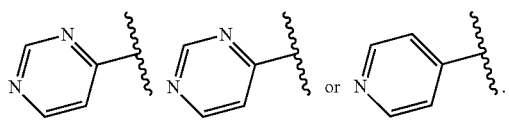

The term "a two membered ring system containing 1 to 4 heteroatoms selected from S and N, wherein at least one ring is aromatic in nature" is selected from the group consisting of

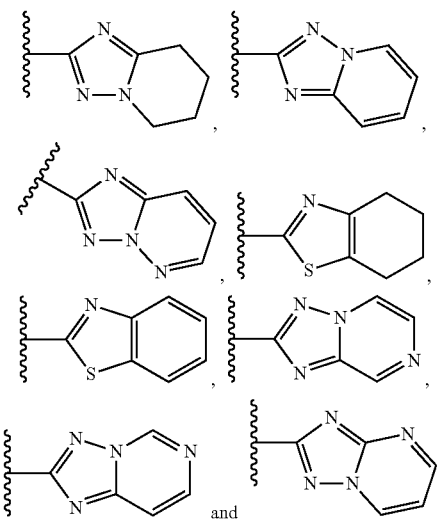

and

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

The present invention provides compounds of formula I, the use of such compounds for the preparation of medicaments for the treatment of Alzheimer's disease, cerebral amyloid angiopathy, hereditary cerebral hemorrhage with amyloidosis, Dutch-type (HCHWA-D), multi-infarct dementia, dementia pugilistica or Down syndrome, their manufacture and medicaments based on a compound of formula I in accordance with the invention.

The invention further provides all forms of optically pure enantiomers, racemates or diastereomeric mixtures for compounds of formula I.

In part, the present invention provides compounds of formula I

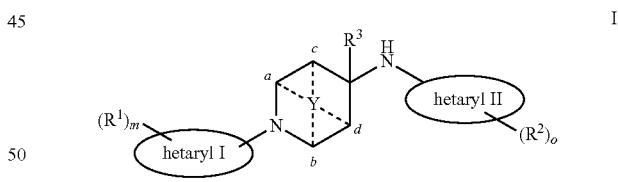

hetaryl I is a five or six membered heteroaryl group, containing 1 to 3 heteroatoms, selected from S and N;

hetaryl II is a six membered heteroaryl group, containing 1 to 3 heteroatoms, selected from S and N, or is a two membered ring system containing 1 to 4 heteroatoms selected from S and N, wherein at least one ring is aromatic in nature;

$R^1$ is lower alkyl, lower alkoxy, lower alkyl substituted by halogen, or halogen;

$R^2$ is lower alkyl, lower alkyl substituted by hydroxy or is $-(CH_2)_p$-phenyl which is optionally substituted by halogen;

$R^3$ is hydrogen or lower alkyl;

Y is $-(CH_2)_n-$, $-CH_2OCH_2-$, $-CH_2O-$, $CH_2S-$, or $-CH_2SCH_2-$ and is bonded to two of the ring carbon atoms, wherein bonding is either to ring carbon atoms a and b or to ring carbon atoms c and d;
p is 0 or 1;
m is 0, 1 or 2; if m is 2 then each R¹ is the same or different;
n is 2 or 3; and
o is 0, 1 or 2, if o is 2, then each R² is the same or different;
or to pharmaceutically active acid addition salts thereof.

An embodiment of the invention provides further compounds of formula I,

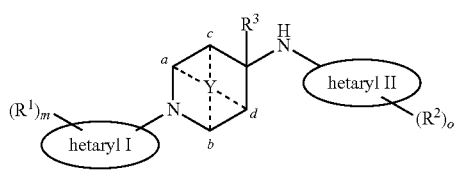

I wherein
hetaryl I is pyridinyl, 1,2,4-thiadiazolyl, pyrazinyl or pyrimidinyl;
hetaryl II is [1,2,4]triazolo[1,5-a]pyridinyl, [1,2,4]triazolo[1,5-a]pyrazinyl, 5,6,7,8-tetrahydro-[1,2,4]triazolo[1,5-a]pyridinyl, [1,2,4]triazolo[1,5-c]pyrimidinyl, 4,5,6,7-tetrahydro-benzothiazolyl or pyrimidinyl;
R¹ is methyl, chloro or CF₃;
R² is methyl, n-propyl, fluoro, chloro, trifluoromethyl, methoxy, —C(CH₃)₂OH, O-benzyl, cyclohexyl substituted by methyl or trifluoromethyl, furyl, or —(CH₂)$_p$-phenyl which is optionally substituted by one, two or three halogen atoms selected from F and Cl, or by cyano or methoxy;
R³ is hydrogen or methyl;
Y is —(CH₂)$_n$—, —CH₂OCH₂—, —OCH₂—, —CH₂SCH₂—, or —SCH₂ and is bonded to two of the ring carbon atoms, wherein bonding is either to ring carbon atoms a and b or to ring carbon atoms c and d;
p is 0 or 1;
m is 0, 1 or 2;
n is 2, or 3; and
o is 1 or 2, if o is 2, then each R² is the same or different;
or pharmaceutically active acid addition salts thereof.

One embodiment of the invention provides further compounds of formula I, wherein Y is —(CH₂)₂—, hetaryl I is

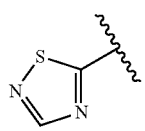 [SMILES: *c1ncns1]

and hetaryl II is a two membered ring system containing 1 to 4 heteroatoms, for example the following compounds
[(rac)-3-exo-8-(3-methyl-[1,2,4]thiadiazol-5-yl)-8-aza-bicyclo[3.2.1]oct-3-yl]-(4-phenyl-4,5,6,7-tetrahydro-benzothiazol-2-yl)-amine;
[(rac)-8-endo-3-(3-Methyl-[1,2,4]thiadiazol-5-yl)-3-aza-bicyclo[3.2.1]oct-8-yl]-[8-(2-chloro-4-fluoro-phenyl)-6-methyl-[1,2,4]triazolo[1,5-a]pyridin-2-yl]-amine;
[(rac)-8-endo-3-(3-Methyl-[1,2,4]thiadiazol-5-yl)-3-aza-bicyclo[3.2.1]oct-8-yl]-[8-(2-chloro-4-fluoro-phenyl)-6-fluoro-[1,2,4]triazolo[1,5-a]pyridin-2-yl]-amine;
[(rac)-8-endo-3-(3-Methyl-[1,2,4]thiadiazol-5-yl)-3-aza-bicyclo[3.2.1]oct-8-yl]-[8-(4-chloro-2-methoxy-phenyl)-[1,2,4]triazolo[1,5-a]pyridin-2-yl]-amine;
[(rac)-8-endo-3-(3-Methyl-[1,2,4]thiadiazol-5-yl)-3-aza-bicyclo[3.2.1]oct-8-yl]-[8-(3-cyano-4-fluoro-phenyl)-[1,2,4]triazolo[1,5-a]pyridin-2-yl]-amine;
[(rac)-8-endo-3-(3-Methyl-[1,2,4]thiadiazol-5-yl)-3-aza-bicyclo[3.2.1]oct-8-yl]-[8-(3,4-difluoro-phenyl)-6-trifluoromethyl-[1,2,4]triazolo[1,5-a]pyridin-2-yl]-amine;
[(rac)-8-endo-3-(3-Methyl-[1,2,4]thiadiazol-5-yl)-3-aza-bicyclo[3.2.1]oct-8-yl]-[8-methoxy-[1,2,4]triazolo[1,5-a]pyridin-2-yl]-amine;
[(rac)-8-endo-3-(3-Methyl-[1,2,4]thiadiazol-5-yl)-3-aza-bicyclo[3.2.1]oct-8-yl]-[8-chloro-6-trifluoromethyl-[1,2,4]triazolo[1,5-a]pyridin-2-yl]-amine;
[(rac)-8-endo-3-(3-Methyl-[1,2,4]thiadiazol-5-yl)-3-aza-bicyclo[3.2.1]oct-8-yl]-[5,6-dimethyl-[1,2,4]triazolo[1,5-a]pyridin-2-yl]-amine;
[(rac)-8-endo-3-(3-Methyl-[1,2,4]thiadiazol-5-yl)-3-aza-bicyclo[3.2.1]oct-8-yl]-[8-benzyloxy-[1,2,4]triazolo[1,5-a]pyridin-2-yl]-amine;
[(rac)-8-endo-3-(3-Methyl-[1,2,4]thiadiazol-5-yl)-3-aza-bicyclo[3.2.1]oct-8-yl]-[5-propyl-[1,2,4]triazolo[1,5-a]pyridin-2-yl]-amine;
[(rac)-8-endo-3-(3-Methyl-[1,2,4]thiadiazol-5-yl)-3-aza-bicyclo[3.2.1]oct-8-yl]-(5-phenyl-[1,2,4]triazolo[1,5-a]pyrazin-2-yl)-amine;
[(rac)-8-endo-3-(3-Methyl-[1,2,4]thiadiazol-5-yl)-3-aza-bicyclo[3.2.1]oct-8-yl]-[5-trifluoromethyl-[1,2,4]triazolo[1,5-a]pyridin-2-yl]-amine;
[(rac)-8-endo-3-(3-Methyl-[1,2,4]thiadiazol-5-yl)-3-aza-bicyclo[3.2.1]oct-8-yl]-[6-chloro-8-(3,4-difluoro-phenyl)-[1,2,4]triazolo[1,5-a]pyridin-2-yl]-amine;
[(rac)-8-endo-3-(3-Methyl-[1,2,4]thiadiazol-5-yl)-3-aza-bicyclo[3.2.1]oct-8-yl]-[7-methyl-5-propyl-[1,2,4]triazolo[1,5-c]pyrimidin-2-yl]-amine;
[(rac)-8-endo-3-(3-Methyl-[1,2,4]thiadiazol-5-yl)-3-aza-bicyclo[3.2.1]oct-8-yl]-[8-(4,4-dimethyl-cyclohexyl)-[1,2,4]triazolo[1,5-a]pyridin-2-yl]-amine;
[(rac)-8-endo-3-(3-Methyl-[1,2,4]thiadiazol-5-yl)-3-aza-bicyclo[3.2.1]oct-8-yl]-(7-furan-2-yl-[1,2,4]triazolo[1,5-a]pyrimidin-2-yl)-amine;
[(rac)-8-endo-3-(3-Methyl-[1,2,4]thiadiazol-5-yl)-3-aza-bicyclo[3.2.1]oct-8-yl]-[7-trifluoromethyl-[1,2,4]triazolo[1,5-a]pyridin-2-yl]-amine;
[(rac)-8-endo-3-(3-Methyl-[1,2,4]thiadiazol-5-yl)-3-aza-bicyclo[3.2.1]oct-8-yl]-[8-(4-trifluoromethyl-cyclohexyl)-[1,2,4]triazolo[1,5-a]pyridin-2-yl]-amine;
[(rac)-8-(4-Fluoro-phenyl)-5,6,7,8-tetrahydro-[1,2,4]triazolo[1,5-a]pyridin-2-yl]-[(rac)-8-exo-3-(3-methyl-[1,2,4]thiadiazol-5-yl)-3-aza-bicyclo[3.2.1]oct-8-yl]-amine; and
[(rac)-8-(3,4-Difluoro-phenyl)-5,6,7,8-tetrahydro-[1,2,4]triazolo[1,5-a]pyridin-2-yl]-[(rac)-8-endo-3-(3-methyl-[1,2,4]thiadiazol-5-yl)-3-aza-bicyclo[3.2.1]oct-8-yl]-amine.

A further embodiment of the invention provides compounds of formula I wherein Y is —(CH₂)₂—, hetaryl I is

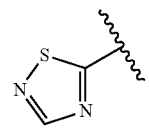 [SMILES: *c1ncns1]

and hetaryl II is a six membered heteroaryl group, containing 1 to 3 heteroatoms, selected from S and N, for example the following compound 2-{6-(4-chloro-benzyl)-2-[(rac)-3-endo-8-(3-methyl-[1,2,4]
thiadiazol-5-yl)-8-aza-bicyclo[3.2.1]oct-3-ylamino]-pyrimidin-4-yl}-propan-2-ol.

A further embodiment of the invention provides compounds of formula I wherein Y is —(CH$_2$)$_n$—, hetaryl I is

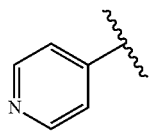

and hetaryl II is a two membered ring system containing 1 to 4 heteroatoms, for example the following compounds

[(rac)-3-exo-8-(2-chloropyridin-4-yl)-8-aza-bicyclo[3.2.1]
oct-3-yl]-[8-(3,4-difluorophenyl)-6-methyl-[1,2,4]triazolo[1,5-a]pyridin-2-yl]-amine and

[8-(3,4-difluoro-phenyl)-[1,2,4]triazolo[1,5-a]pyridin-2-yl]-
[(rac)-8-endo-3-(2-trifluoromethyl-pyridin-4-yl)-3-aza-bicyclo[3.2.1]oct-8-yl]-amine.

A further embodiment of the invention provides compounds of formula I wherein heteroaryl I is

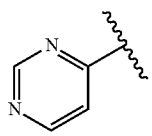

and hetaryl II is a two membered ring system containing 1 to 4 heteroatoms, for example the following compounds

[(rac)-8-endo-3-(6-methyl-pyrimidin-4-yl)-3-aza-bicyclo
[3.2.1]oct-8-yl]-[8-(2,3,4-trifluoro-phenyl)-[1,2,4]triazolo[1,5-a]pyridin-2-yl]-amine;

[(rac)-8-endo-3-(6-Methyl-pyrimidin-4-yl)-6-oxa-3-aza-bicyclo[3.2.1]oct-8-yl]-[8-(2,3,4-trifluoro-phenyl)-[1,2,4]
triazolo[1,5-a]pyridin-2-yl]-amine;

[(rac)-9-exo-7-(6-Methyl-pyrimidin-4-yl)-3-thia-7-aza-bicyclo[3.3.1]non-9-yl]-[8-(2,3,4-trifluoro-phenyl)-[1,2,4]
triazolo[1,5-a]pyridin-2-yl]-amine;

[(rac)-9-endo-3-(6-Methyl-pyrimidin-4-yl)-3-aza-bicyclo
[3.3.1]non-9-yl]-[8-(2,3,4-trifluoro-phenyl)-[1,2,4]triazolo[1,5-a]pyridin-2-yl]-amine;

[(rac)-9-exo-7-(6-Methyl-pyrimidin-4-yl)-3-oxa-7-aza-bicyclo[3.3.1]non-9-yl]-[8-(2,3,4-trifluoro-phenyl)-[1,2,4]
triazolo[1,5-a]pyridin-2-yl]-amine;

[(rac)-8-exo-Methyl-3-(6-methyl-pyrimidin-4-yl)-3-aza-bicyclo[3.2.1]oct-8-endo-yl]-[8-(2,3,4-trifluoro-phenyl)-[1,2,4]triazolo[1,5-a]pyridin-2-yl]-amine; and

[8-(3,4-Difluoro-phenyl)-[1,2,4]triazolo[1,5-a]pyridin-2-
yl]-[(rac)-8-endo-3-(2-methyl-pyrimidin-4-yl)-3-aza-bicyclo[3.2.1]oct-8-yl]-amine.

The present compounds of formula I and their pharmaceutically acceptable salts can be prepared by methods known in the art, for example, by processes described below, which processes comprise a) reacting a compound of formula

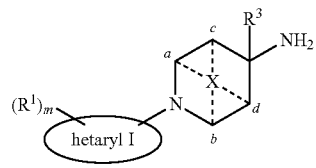

with a compound of formula

to obtain a compound of formula

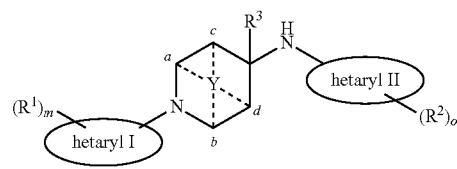

wherein X is halogen and the further groups have the meaning as described above and,
    if desired, converting the compounds obtained into pharmaceutically acceptable acid addition salts;
or
    b) reacting a compound of formula

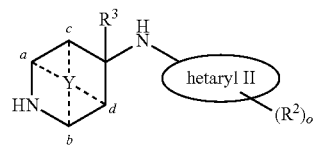

with a compound of formula

to obtain a compound of formula

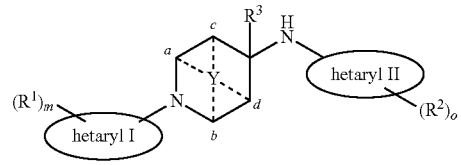

wherein X is halogen and the further groups have the meaning as described above, or c) reacting a compound of formula

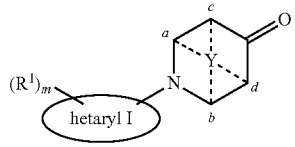

with a compound of formula

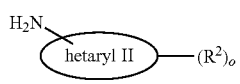

to obtain a compound of formula

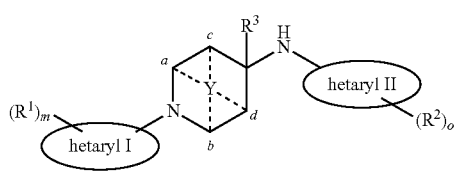

wherein the groups have the meaning as described above and $R^3$ is hydrogen, and, if desired converting the compounds obtained into pharmaceutically acceptable acid addition salts.

The preparation of compounds of formula I of the present invention can be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in the examples, or by methods known in the art.

Scheme 1

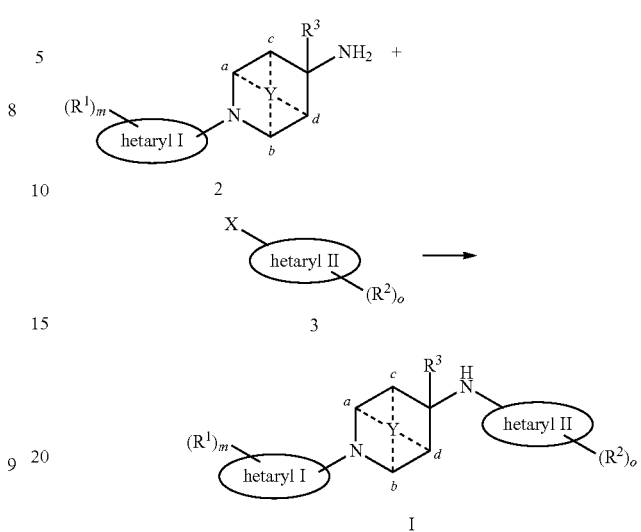

The present compounds of formula I and their pharmaceutically acceptable salts can be prepared by coupling of amines of formula 2 and halides of formula 3 (see Scheme 1). This reaction can be accomplished using generally known procedures, e.g. displacement reactions under catalytic conditions (like e.g. palladium(0) or copper(II) catalysis) or under thermal conditions or under basic conditions.

Scheme 2

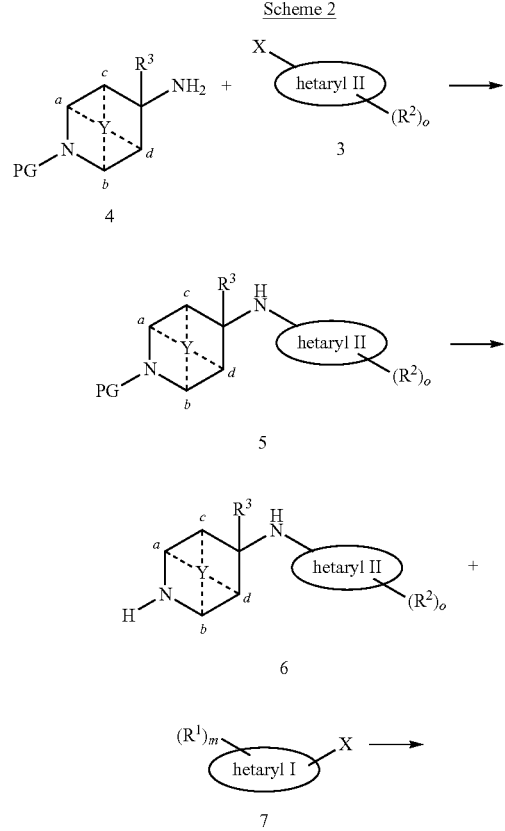

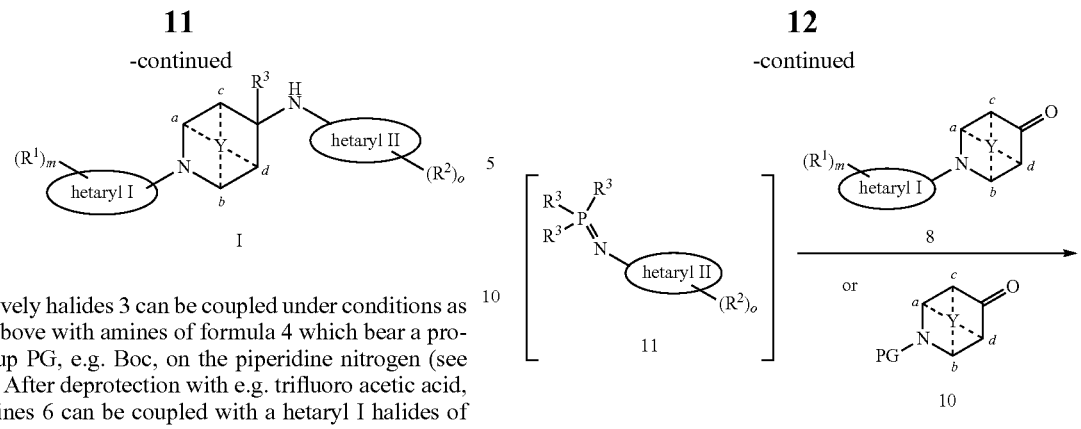

Alternatively halides 3 can be coupled under conditions as described above with amines of formula 4 which bear a protective group PG, e.g. Boc, on the piperidine nitrogen (see Scheme 2). After deprotection with e.g. trifluoro acetic acid, the piperidines 6 can be coupled with a hetaryl I halides of formula 7 to provide compounds of formula I.

Scheme 3

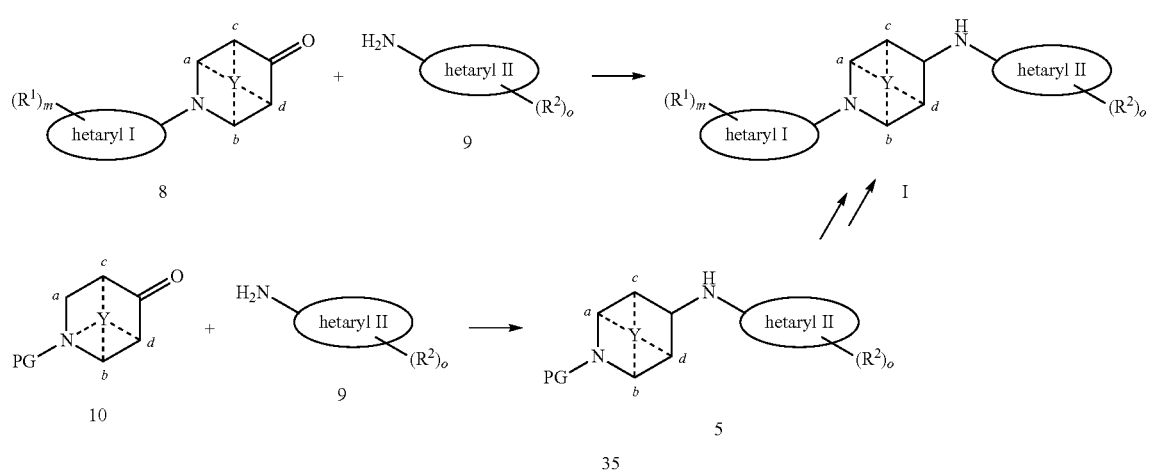

R³ is hydrogen;

Alternatively anilines of formula 9 can be employed in a reductive amination reaction with ketones of formula 8 or 10 (see Scheme 3) providing compounds I either directly or after cleavage of protective group PG of 5, followed by coupling with heteroaryl I halide 7 as described in Scheme 2. The reductive amination can be accomplished by methods known to one skilled in the art of organic synthesis, for example by heating the amine and the ketone in an appropriate solvent (e.g. toluene, dichloroethane, THF) possibly in the presence of an acid (e.g. acetic acid, tetraisopropyl-orthotitanate) and reduction of the intermediary imine with an appropriate reducing agent (e.g. sodium triacetoxyborohydride, sodium cyanoborohydride, sodium borohydride, hydrogen in the presence paladium on charcoal).

Scheme 4

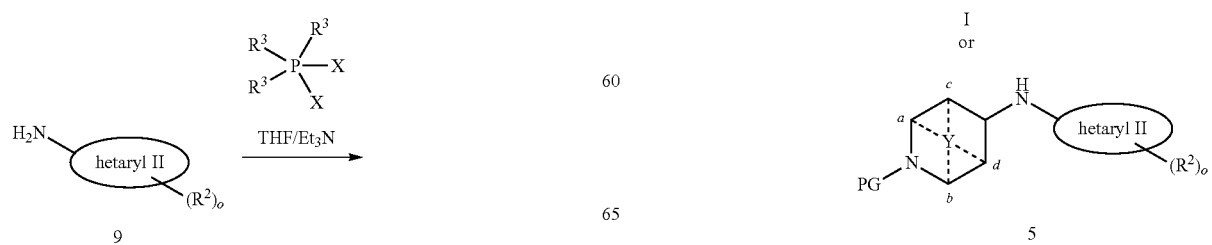

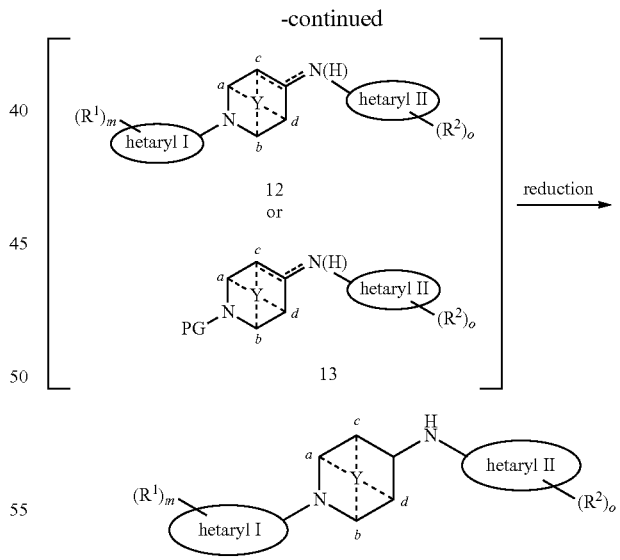

The coupling of anilines of formula 9 with ketones of formula 8 or 10 can alternatively be accomplished by following an aza-Wittig/reduction protocol (see Scheme 4). Anilines of formula 9 can be first converted to their corresponding trialkylphosphazenes 11 by Reaction with trialkyldihalophosphorane (e.g. dichlorotrimethylphosphorane, prepared by reaction of trimethylphosphine with hexachloroethane in THF or dichloromethane) and an organic amine base (e.g. triethylamine, di-isopropylethylamine) in a suitable solvent (e.g. THF, dichloromethane). Ketones of formula 8 or 10 are then added to the reaction mixture containing the in situ prepared phosphazenes 11 and the mixture is heated. The resulting imine/enamines (enamines can be formed for compounds with a bridge Y between atoms a and b) 12 or 13 are then treated with an appropriate reducing agent (e.g. sodium triacetoxyborohydride, sodium cyanoborohydride, sodium borohydride, decaborane, borane-THF complex, hydrogen in the presence palladium on charcoal) in the appropriate solvent (THF, DCM, MeOH and mixtures thereof) with or without acid catalysis (e.g. acetic acid) at ambient or elevated temperatures to provide compounds of formula 5 or I (for $R^3$ being hydrogen).

5a by strong heating (>130° C.) in the presence of a suitably functionalized hydroxylamine derivative e.g. O-(trimethlysilyl)-hydroxylamine in a polar solvent e.g. dimethylacetamide.

Scheme 6

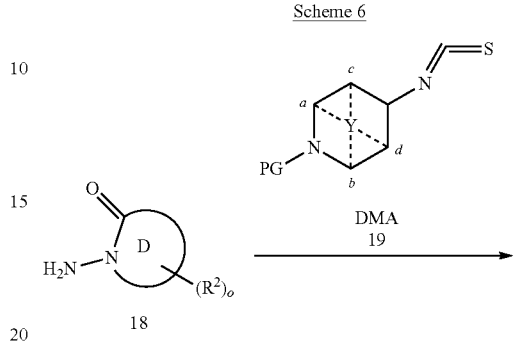

Scheme 5

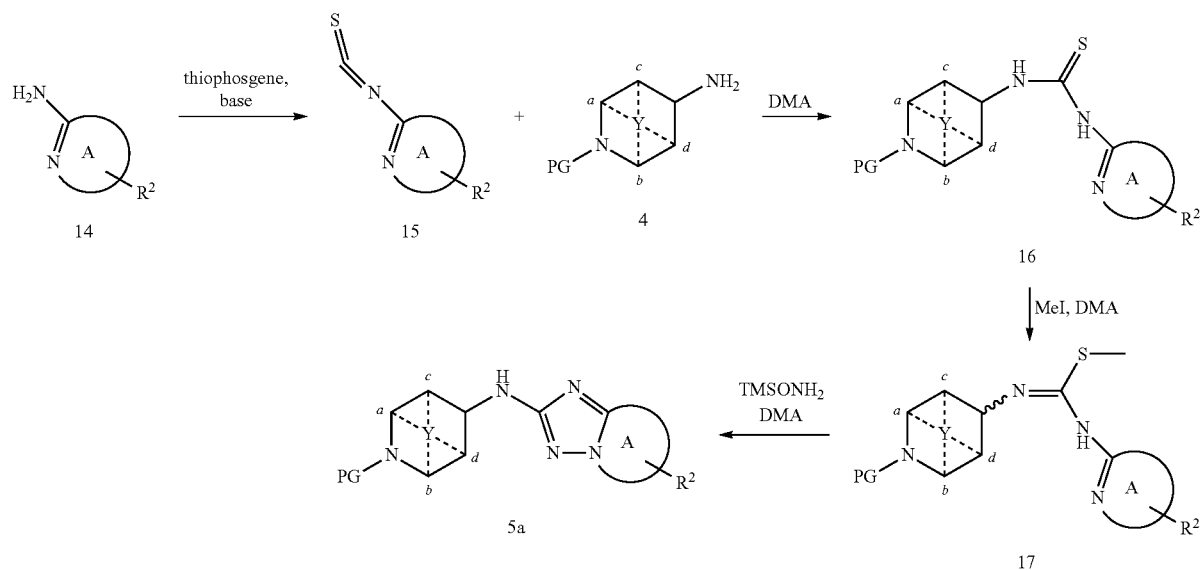

A represents

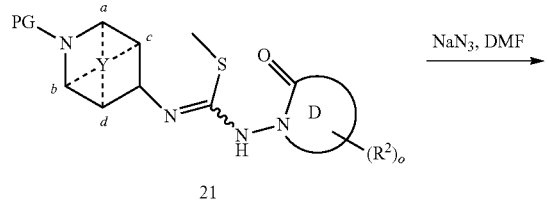

Triazolopyridines of formula 5a can alternatively be constructed by converting amines of formula 14 into their corresponding isothiocyanates 15 (e.g. by reaction with thiophosgene or 1,1'-thiocarbonyldiimidazole in dichloromethane in the presence of an organic or aqueous inorganic base) and reaction with amines of formula 4 (see Scheme 5). The resulting thioureas 16 can be activated by alkylation with iodomethane and subsequently cyclized to triazolopyridines

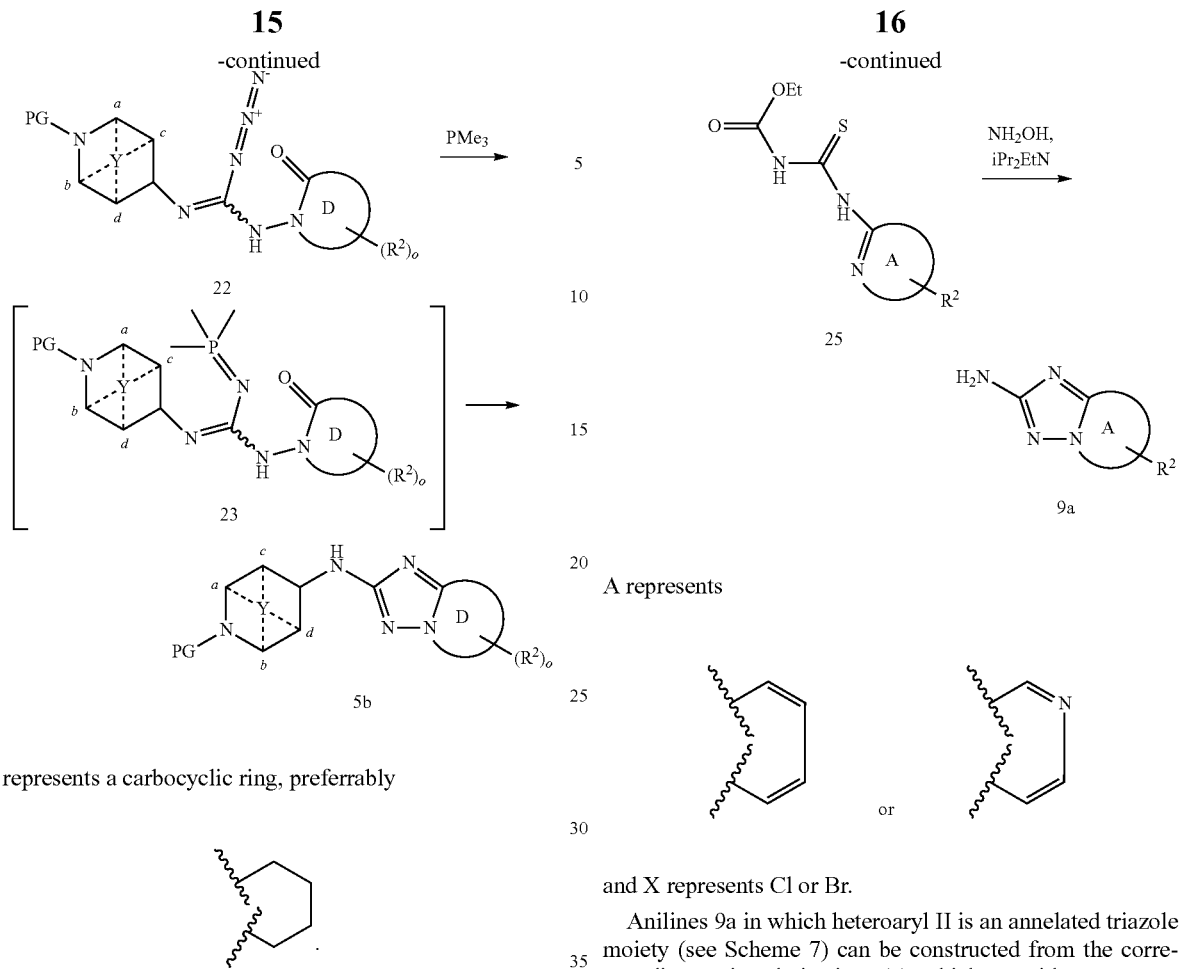

D represents a carbocyclic ring, preferrably

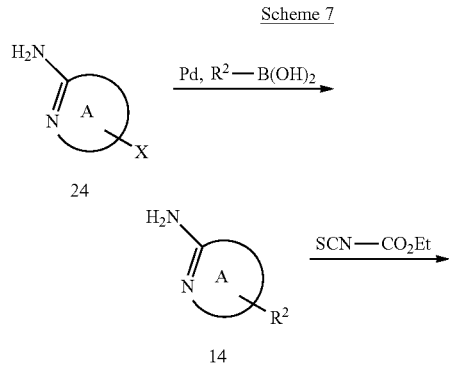

Triazolopyridines of formula 5b can be prepared by first condensing cyclic hydrazides 18 and isothiocyanates 19 (prepared by known methods to those skilled in the art) to form thiourea 20 (see Scheme 6). Activation of the sulphur group by alkylation (e.g. iodomethane in DMF at elevated temperatures) allows its displacement by an azide (e.g. sodium azide in DMF at elevated temperatures) to afford azidoguanidine 22. Staudinger reduction with trimethylphosphine generates an intermediate phosphazene 23 which cyclises on heating to generate triazolopyridine 5b.

Anilines of formula 9, which can be used as starting materials for the preparation of compounds of formula I can be prepared as described in the following schemes.

and X represents Cl or Br.

Anilines 9a in which heteroaryl II is an annelated triazole moiety (see Scheme 7) can be constructed from the corresponding amino derivatives 14, which are either commercially available or can be obtained from the corresponding halides 24 by palladium catalyzed Suzuki coupling with boronic acids or boronic esters (e.g. pinacol ester). Amines 14 can be reacted with ethoxycarbonyl isothiocyanate to yield thiourea derivatives 25 which undergo a cyclization reaction upon treatment with hydroxylamine in the presence of a base under liberation of carbon dioxide to yield annelated triazoles 9a (as e.g. described by M. Nettekoven et al., Synthesis 2003, 11, 1649-1652).

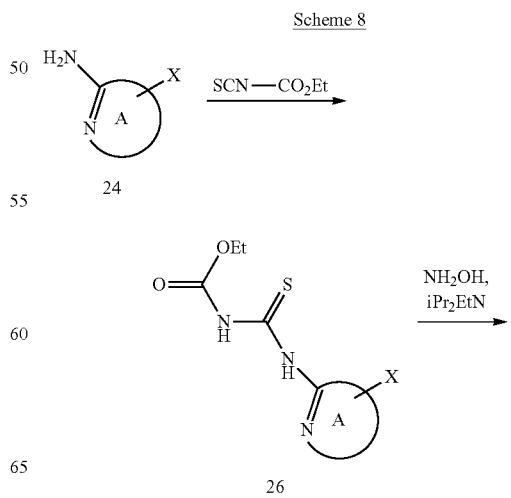

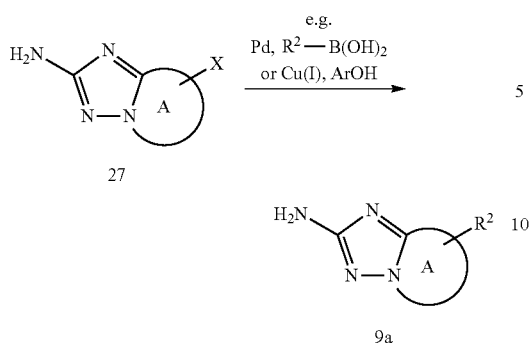

A represents

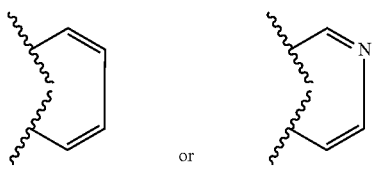 [SMILES: */C=C\C=C/* ; */C=C\N=C/*]

and X represents Cl or Br.

Alternatively the order of steps in Scheme 7 can be changed (see Scheme 8). Halides 24 (which are either commercially available or can be synthesized by methods known in the art) can be reacted with ethoxycarbonyl isothiocyanate followed by treatment with hydroxylamine to provide annelated triazoles 27. These halides can then be subjected e.g. to palladium catalyzed Suzuki coupling with boronic acids or copper (I) catalyzed coupling with phenols (e.g. according to D. Maiti et al. JOC 2010, 75, 1791-1794) to provide substituted aminotriazoles 9a.

Scheme 9

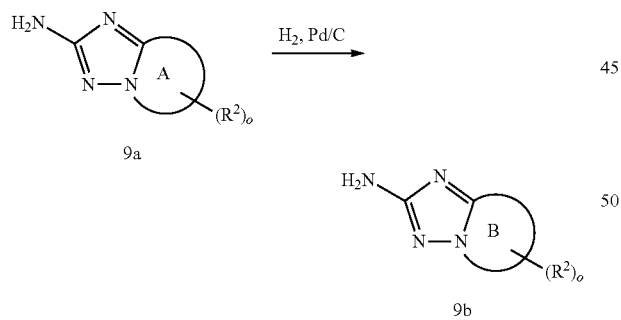

A is

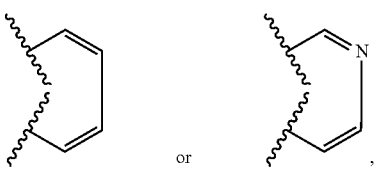 [SMILES: */C=C\C=C/* ; */C=C\N=C/*]

B is

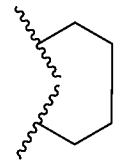

Compounds 9a can be hydrogenated with palladium on charcoal as catalyst to yield the corresponding partly saturated compounds 9b (see Scheme 9). Depending on the nature of ring A this reaction may require elevated temperature or hydrogen pressure or the presence of acid (e.g. HCl). Alternatively compounds 9a can be reduced with metals e.g. magnesium in alcoholic solution (like ethanol) with or without activation of the metal (e.g. activation with catalytic amounts of iodine).

Scheme 10

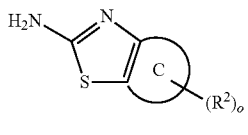

C represents a carbocyclic ring, preferably

Anilines 9c in which heteroaryl II is a an annelated thiazole (see Scheme 10) can be prepared by condensation of •-bromoketones 28 with thiourea (for example by heating in an appropriate solvent, e.g. ethanol). •-Bromoketones are either commercially available or readily prepared by methods known to one skilled in the art of organic synthesis, e.g. by reaction of an appropriate ketone with bromine in chloroform.

Halides of formula 3, which can be used as starting materials for the preparation of compounds of formula I can be prepared as described in the following schemes.

Scheme 11

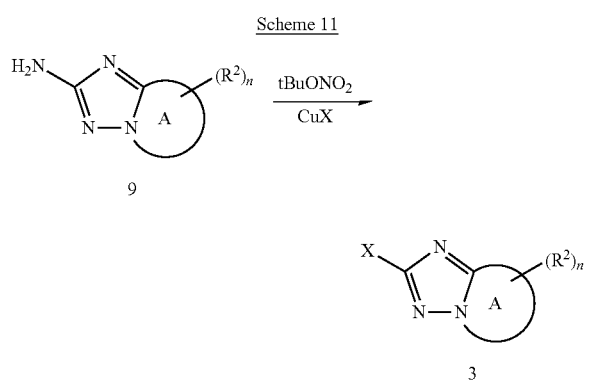

The halotriazole 3 can be prepared from the aniline 9 (see Scheme 11) via formation of the corresponding diazonium salt and subsequent decomposition in the presence of a halide source like copper (I) halide or hydrogenhalide (X=chlorine or bromine).

Scheme 12

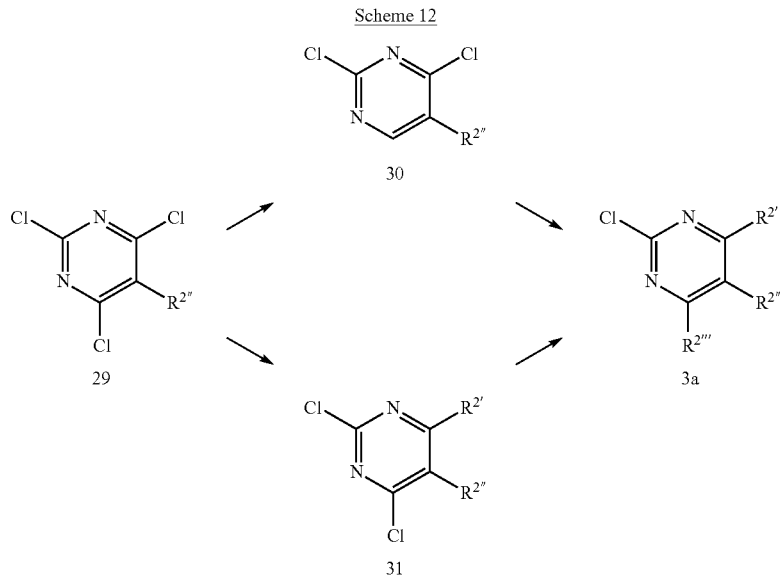

$R^{2'}$, $R^{2''}$ and $R^{2'''}$ is lower alkyl, lower alkyl substituted by hydroxy or is —$(CH_2)_p$-phenyl, optionally substituted by halogen Halides 3a in which heteroaryl II is a pyrimidine (see Scheme 12) can be prepared as e.g. described in K. Baumann et al., WO2009103652 by reduction of trichloro-pyrimidines 29 to give dichloro-derivative 30, e.g. by treatment with zink in aqueous ammonia at 0° C. Subsequently, the 4-chloro substituent of 30 can be replaced in a nucleophilic substitution reaction (like reaction with a Grignard reagent $R^{2'}MgX$, e.g. benzylmagnesium chloride in tetrahydrofuran at −80 to +20° C.) or, by a metal catalyst assisted displacement reaction (e.g. using palladium acetate, 2-(dicyclohexylphosphino-biphenyl, tetrahydrofuran, microwave oven, 30 min, 200° C.). Alternatively, one of the reactive chloro atoms of 29 is first replaced by a group $R^{2'}$, followed by replacement of a second chloro-substituent in the intermediate 31 by a group $R^{2'''}$, to afford 3a.

Scheme 13

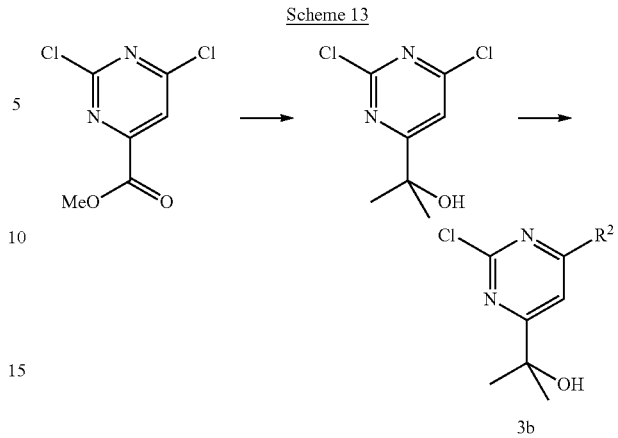

$R^2$ is —$(CH_2)_p$-phenyl, optionally substituted by halogen

Halides 3b in which heteroaryl II is a pyrimidine (see Scheme 13) can be prepared from 2,6-dichloro-pyrimidine-4-carboxylic acid methyl ester by reaction with e.g. methylmagnesium chloride in THF at −78° C. to 0° C. which provides 2-(2,6-dichloro-pyrimidin-4-yl)-propan-2-ol. The chloride in 4-position of 2-(2,6-dichloro-pyrimidin-4-yl)-propan-2-ol can be replaced by a substituent $R^2$ for example in a Suzuki coupling reaction with an aryl/heteroaryl boronic acid/ester $R^2$—$B(OH/OR')_2$ in the presence of a palladium catalyst and a base (e.g. sodium carbonate) in e.g. dimethoxyethane as solvent to provide chloride 3b. Alternatively the 4-chloro substituent can be reacted with an organo zinc chloride $R^2ZnCl$, e.g. benzylzinc chloride in the presence of a palladium catalyst to provide chloride 3b. To accomplish these modifications it might be necessary to protect the alcohol group of 2-(2,6-dichloro-pyrimidin-4-yl)-propan-2-ol prior to the second step e.g. by protection with trimethylsilyl group which can be introduced e.g. with bis(trimethylsilyl)acetamide and can be cleaved after the modifications with e.g. p-TsOH in THF/water.

Ketones of formula 8, which can be used as starting materials for the preparation of compounds of formula I can be prepared as described in the following schemes.

Scheme 14

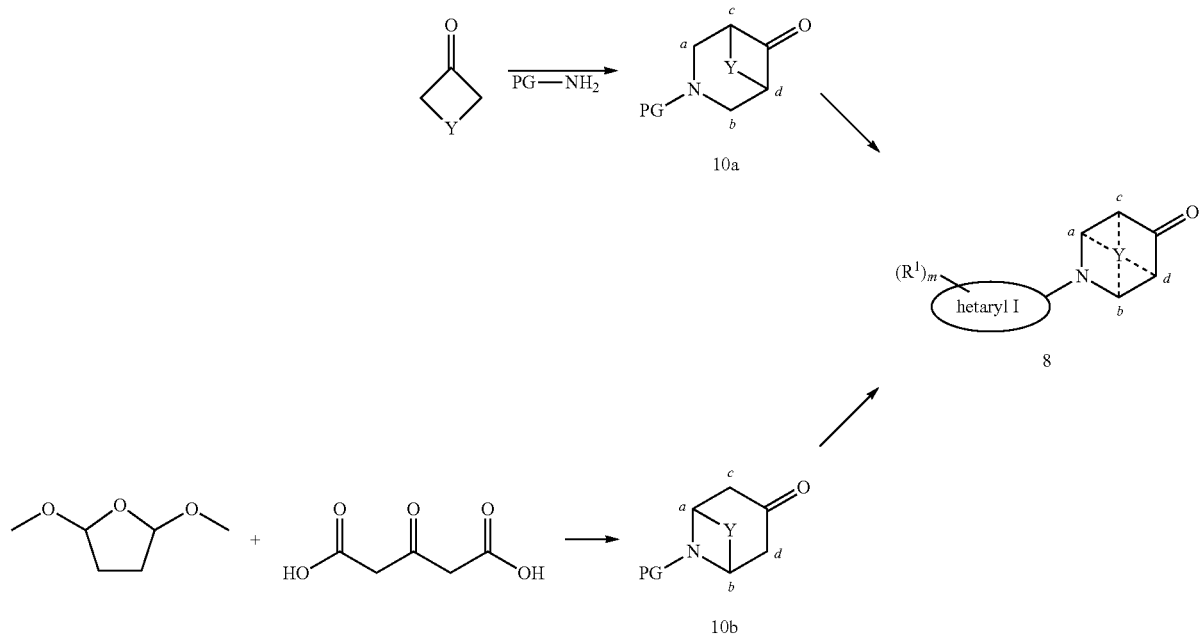

Mannich reaction of the ketone in scheme 14 with formaldehyde and an appropriate amine PG-NH$_2$ yields the ketone 10a. The protection group of 10a can be changed as appropriate (e.g. from benzyl to boc-protection). Condensation of 2,5-dimethoxy-tetrahydrofurane with the biacid in the presence of an appropriate amine PG-N$_2$ provides the ketone 10b. Deprotection of 10b or 10a and coupling with an appropriate hetaryl I halide under basic, thermal or metal catalyzed conditions yields the ketone 8.

Amines of formula 2, which can be used as starting materials for the preparation of compounds of formula I can be prepared as described in the following schemes.

Scheme 15

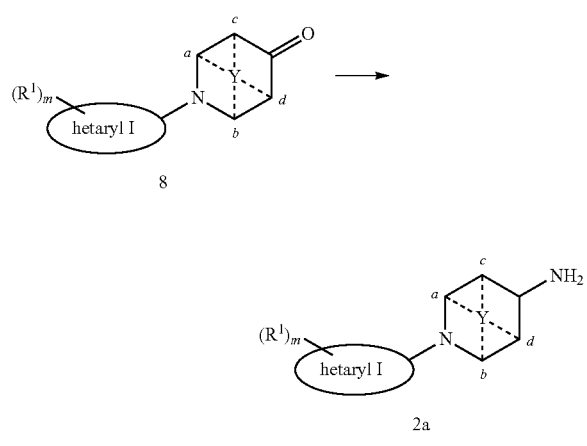

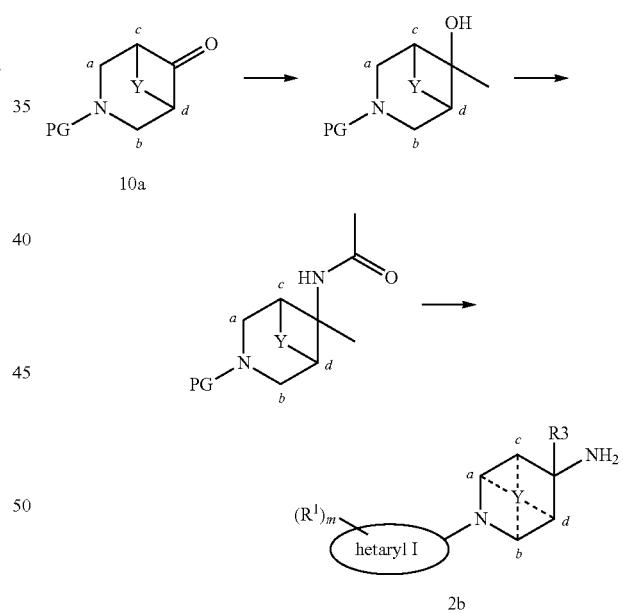

The ketones 8 can be easily converted into the amines 2a (R$^3$=H) via reductive amination with ammonia, or hydroxylamine or other suitable amine precursor (see Scheme 15). Preparation of amine 2b (R$^3$=Me) starts with the Grignard addition of a methyl grignard reagent to the ketone 10a. The resulting tertiary alcohol undergoes a Ritter reaction with acetonitrile under strong acidic conditions. Saponification of the amide and changing of the protection group to the hetaryl I group as previously described in scheme 14 yields the amine 2b.

Scheme 16

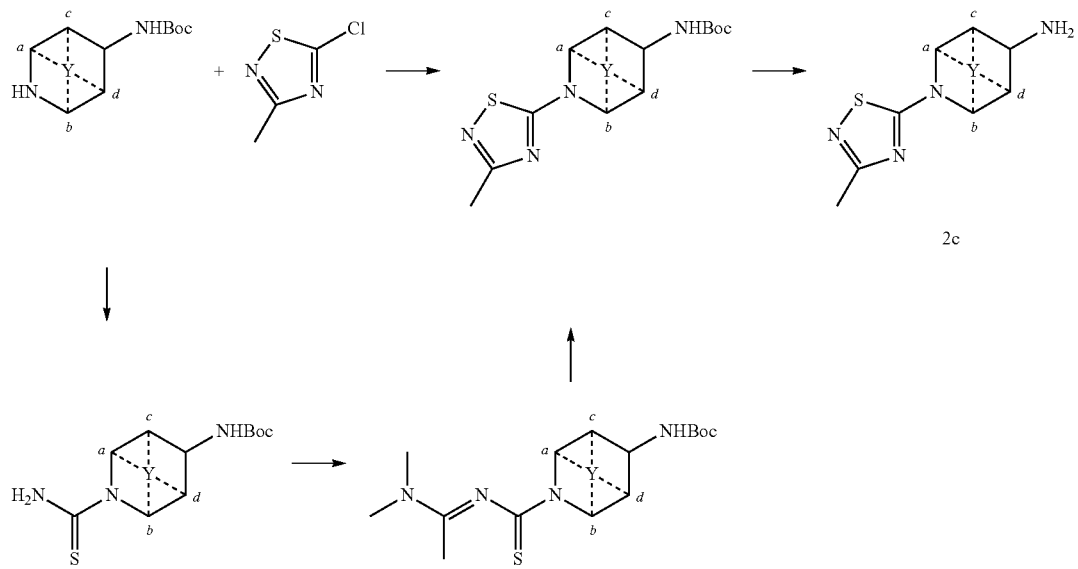

Amines 2c in which heteroaryl I is a 3-methyl-[1,2,4]thiadiazole (see Scheme 15) can e.g. be prepared by palladium catalyzed coupling of 5-chloro-3-methyl-[1,2,4]thiadiazole with piperidin-4-yl-carbamic acid tert-butyl esters and subsequent cleavage of the Boc-protective group in the presence of an acid. Alternatively amines 2c can be prepared from the Boc-protected aminopiperidines by reaction with an isothiocyanate source like benzoylisothiocyanate, metal isothiocyanate, thiophosgen or an activated thiourea derivative to give the corresponding thiourea derivatives. Condensation with 1,1-dimethoxy-ethyl)-dimethyl-amine and subsequent cyclization with hydroxylamine-O-sulfonic acid in the presence of a base like pyridine yields after deprotection the amines 2c.

Scheme 17

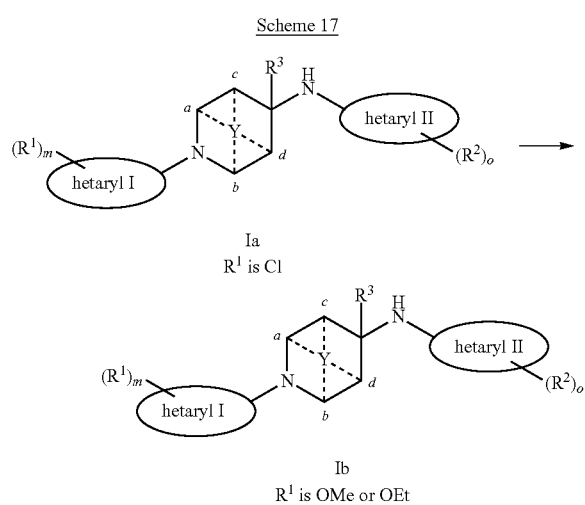

Compounds of formula Ia where $R^1$ is a halogen such as Cl can be converted into compounds of formula Ib where $R^1$ is alkoxy, such as OMe, OEt upon treatment with the appropriate sodium salt (NaOMe or NaOEt) in a suitable alcohol solvent such as methanol or ethanol respectively (see Scheme 17).

The compounds were investigated in accordance with the test given hereinafter.

Description of γ-Secretase Assay

Cellular γ-Secretase Assay

Human neuroglioma H4 cells overexpressing human APP were plated at 30,000 cells/well/200 μL in 96-well plates in IMDM media containing 10% FCS, 0.2 mg/L Hygromycin B and incubated for 2 hours at 37° C., 5% $CO_2$ prior to adding test compounds.

Compounds for testing were dissolved in 100% $Me_2SO$ yielding in a 10 mM stock solution. Typically 12 μL of these solutions were further diluted in 1000 μL of IMDM media (w/o FCS). Subsequent 1:1 dilutions gave a ten point dose response curve. 100 μL of each dilution was added to the cells in 96-well plates. Appropriate controls using vehicle only and reference compound were applied to this assay. The final concentration of $Me_2SO$ was 0.4%.

After incubation for 22 hours at 37° C., 5% $CO_2$, 50 μL supernatant was transferred into round-bottom 96-well polypropylene plates for detection of Aβ42. 50 μL assay buffer (50 mM Tris/Cl, pH 7.4, 60 mM NaCl, 0.5% BSA, 1% TWEEN 20) was added to the wells followed by the addition of 100 μL of detection antibody (ruthenylated BAP15 0.0625 μg/mL in assay buffer). 50 μL of a premix of capture antibody (biotinylated 6E10 antibody, 1 μg/mL) and Steptavidin-coated magnetic beads (Dynal M-280, 0.125 mg/mL) were preincubated for 1 hour at room temperature before adding the assay plates. Assay plates were incubated on a shaker for 3 hours at room temperature and finally read in the Bioveris M8 Analyser according to the manufacturer's instructions (Bioveris).

Toxicity of compounds was monitored by a cell viability test of the compound-treated cells using a colorimetric assay (CellTiter 96™ AQ assay, Promega) according to the manufacturer's instructions. Briefly, after removal of 50 μL cell culture supernatant for detection of Aβ42, 20 μL of 1×MTS/PES solution was added to the cells and incubated for 30 minutes at 37° C., 5% $CO_2$. Optical density was then recorded at 490 nm.

$IC_{50}$ values for inhibition of Aβ42 secretion were calculated by nonlinear regression fit analysis using XLfit 4.0 software (IDBS).

In the list below are described the data for all compounds to the inhibition of Aβ42 secretion (μM):

| Example No. | $EC_{50}$ Aβ42 (μM) |
|---|---|
| 1 | 2.95 |
| 2 | 0.41 |
| 3 | 3.37 |
| 4 | 0.627 |
| 5 | 0.273 |
| 6 | 0.179 |
| 7 | 0.175 |
| 8 | 0.199 |
| 9 | 0.232 |
| 10 | 0.296 |
| 11 | 0.428 |
| 12 | 0.833 |
| 13 | 0.557 |
| 14 | 0.215 |
| 15 | 0.217 |
| 16 | 0.235 |
| 17 | 0.273 |
| 18 | 0.158 |
| 19 | 0.42 |
| 20 | 0.289 |
| 21 | 0.553 |
| 22 | 0.623 |
| 23 | 0.917 |
| 24 | 0.300 |
| 25 | 3.237 |
| 26 | 3.833 |
| 27 | 0.643 |
| 28 | 0.642 |

The compounds of formula I and the pharmaceutically acceptable salts of the compounds of formula I can be used as therapeutics, e.g. in the form of pharmaceutical compositions. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, parenterally, e.g. in the form of injection solutions.

The compounds of formula I can be processed with pharmaceutically inert, inorganic or organic carriers for the production of pharmaceutical compositions. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are, however, usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides pharmaceutical compositions containing a compound of formula I or a pharmaceutically acceptable salt thereof and a therapeutically inert carrier, and a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the inhibition of Aβ42 secretion, such as of Alzheimer's disease.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof. The daily dosage can be administered as single dose or in divided doses and, in addition, the upper limit can also be exceeded when this is found to be indicated.

| Tablet Formulation (Wet Granulation) | | | | | |
|---|---|---|---|---|---|
| | | | mg/tablet | | |
| Item | Ingredients | 5 | 25 | 100 | 500 |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | | |
|---|---|---|---|---|---|
| | | | mg/capsule | | |
| Item | Ingredients | 5 | 25 | 100 | 500 |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

EXAMPLE 1

[(rac)-3-exo-8-(2-Chloropyridin-4-yl)-8-aza-bicyclo[3.2.1]oct-3-yl]-[8-(3,4-difluorophenyl)-6-methyl-[1,2,4]triazolo[1,5-a]pyridin-2-yl]-amine

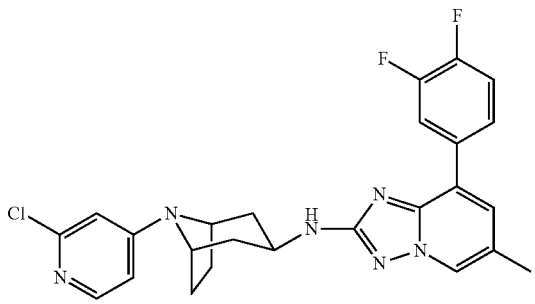 [SMILES: Cc1cc(-c2ccc(F)c(F)c2)c2nc(NC3CC4CCC(C3)N4c3ccnc(Cl)c3)nn2c1]

a) 3-(3,4-Difluorophenyl)-5-methylpyridin-2-amine

3-Bromo-5-methylpyridin-2-amine (0.5 g, 2.7 mmol), 3,4-difluorophenylboronic acid (0.5 g, 3.2 mmol) and [1,1'-bis(diphenylphosphino)ferrocene]dichloropalladium(II)-dichloromethane complex (0.1 g, 0.1 mmol) were dissolved in a mixture of dioxane (10 mL) and 1M aqueous sodium carbonate solution (8 mL) under argon and the mixture was heated to 100° C. for 1 hour. The reaction was diluted with ethyl acetate, separated and the organic layer was washed with brine, dried with sodium sulfate, filtered and the solvent evaporated under reduced pressure. The residue was purified by column chromatography on silica gel using n-heptane/ethyl acetate (v/v 1:1) as eluent. The title compound was obtained as a light brown crystalline solid (0.6 g, quant.).

MS ISP (m/e): 221.2 [(M+H)$^+$].

$^1$H NMR (CDCl$_3$, 400 MHz): δ (ppm)=7.95 (s, 1H), 7.32-7.16 (m, 4H), 4.50 (brs, 2H), 2.38 (s, 3H).

b) 3-(3,4-Difluorophenyl)-2-isothiocyanato-5-methylpyridine

To a solution of 3-(3,4-difluorophenyl)-5-methylpyridin-2-amine (0.6 g, 2.7 mmol) in dichloromethane (15 mL) was added a solution of sodium bicarbonate (2.3 g, 26.7 mmol) in water (25 mL) followed by a solution of thiophosgene (0.25 mL, 3.2 mmol) in dichloromethane (1 mL) and the mixture stirred for 15 minutes. The phases were separated and the organic phase was dried with sodium sulfate and the solvent was evaporated in vacuo to afford the title compound was obtained as a crystalline yellow solid (0.7 g, 100%).

MS ISP (m/e): 263.2 [(M+H)$^+$].

$^1$H NMR (CDCl$_3$, 400 MHz): δ (ppm)=8.27 (s, 1H), 7.50 (s, 1H), 7.32-7.25 (m, 2H), 7.22-7.18 (m, 1H), 2.39 (s, 3H).

c) 1-((rac)-3-exo-8-Benzyl-8-azabicyclo[3.2.1]octan-3-yl)-3-(3-(3,4-difluorophenyl)-5-methylpyridin-2-yl)thiourea To a solution of 3-(3,4-difluorophenyl)-2-isothiocyanato-5-methylpyridine (0.3 g, 1.1 mmol) in dimethylacetamide (0.2 mL) was added (rac)-3-exo-8-benzyl-8-azabicyclo[3.2.1]octan-3-amine (0.3 g, 1.1 mmol) and the mixture was heated to 50° C. for 15 minutes. The reaction was diluted with ethyl acetate, washed with water, brine, dried with sodium sulfate and the solvent was partially evaporated under reduced pressure resulting in the product crystallising. The title compound was obtained as an off-white crystalline solid (0.4 g, 75%).

MS ISP (m/e): 479.3 [(M+H)$^+$].

$^1$H NMR (CDCl$_3$, 400 MHz): δ (ppm)=12.57 (brs, 1H), 12.24 (d, 1H), 8.21 (s, 1H), 7.89-7.82 (m, 3H), 7.47-7.44 (m, 3H), 7.35-7.30 (m, 2H), 7.21-7.16 (m, 1H), 7.13-7.09 (m, 1H), 4.97-4.86 (m, 1H), 4.10 (d, 2H), 3.80 (s, 2H), 2.93 (t, 2H), 2.35-2.17 (m, 8H).

d) Methyl N'-((rac)-3-exo-8-benzyl-8-azabicyclo[3.2.1]octan-3-yl)-N-(3-(3,4-difluorophenyl)-5-methylpyridin-2-yl)carbamimidothioate To a solution of 1-((rac)-3-exo-8-benzyl-8-azabicyclo[3.2.1]octan-3-yl)-3-(3-(3,4-difluorophenyl)-5-methylpyridin-2-yl)thiourea (0.3 g, 0.6 mmol) in dimethylacetamide (1.5 mL) was added iodomethane (0.06 mL, 1.0 mmol) and the mixture was heated to 80° C. for 2 hours. The reaction was evaporated to dryness, the residue redissolved in ethyl acetate, washed with saturated sodium hydrogen carbonate, brine, dried with sodium sulfate, filtered and the solvent evaporated under reduced pressure. The title compound was obtained as a light yellow gum (0.3 g, 94%).

MS ISP (m/e): 493.2 [(M+H)$^+$].

e) ((rac)-3-exo-8-Benzyl-8-azabicyclo[3.2.1]octan-3-yl)-8-(3,4-difluorophenyl)-6-methyl-[1,2,4]triazolo[1,5-a]pyridin-2-amine To a solution of methyl N'-((rac)-3-exo-8-benzyl-8-azabicyclo[3.2.1]octan-3-yl)-N-(3-(3,4-difluorophenyl)-5-methylpyridin-2-yl)carbamimidothioate (0.05 g, 0.1 mmol) in DMF (0.5 mL) was added O-(trimethylsilyl)-hydroxylamine (0.03 mL, 0.2 mmol) and the mixture heated to 150° C. for 1 hour followed by 1 hour at 200° C. in the microwave. The reaction was diluted with ethyl acetate, washed with water, brine, dried with sodium sulfate, filtered and the solvent evaporated under reduced pressure. The residue was purified by column chromatography on silica gel using n-heptane/ethyl acetate (v/v 1:1 to 0:1) as eluent. The title compound was obtained as a light brown gum (0.01 g, 22%).

MS ISP (m/e): 460.2 [(M+H)$^+$].

$^1$H NMR (CDCl$_3$, 400 MHz): δ (ppm)=8.10 (s, 1H), 7.94-7.90 (m, 1H), 7.40-7.16 (m, 1H), 4.93-4.82 (m, 7H), 4.39 (s, 1H), 4.30 (d, 1H), 4.07-3.95 (m, 1H), 3.60 (s, 2H), 3.27 (s, 2H), 2.38 (s, 3H) 2.11-1.99 (m, 4H), 1.83-1.72 (m, 2H), 1.62 (t, 2H).

f) (rac)-3-exo-8-(2-Chloropyridin-4-yl)-8-azabicyclo[3.2.1]octan-3-yl)-8-(3,4-difluorophenyl)-6-methyl-[1,2,4]triazolo[1,5-a]pyridin-2-amine To a solution of ((rac)-3-exo-8-benzyl-8-azabicyclo[3.2.1]octan-3-yl)-8-(3,4-difluorophenyl)-6-methyl-[1,2,4]triazolo[1,5-a]pyridin-2-amine (0.02 g, 0.03 mmol) in methanol (1 mL) was added a spatula tip of 10% palladium on charcoal, followed by a drop of 25% aqueous hydrogen chloride solution and the mixture stirred under an atmosphere of hydrogen (balloon) for 3 hours. The reaction was filtered through Hyflo and concentrated to dryness. The residue was redissolved in dimethylacetamide (1 mL), the mixture made basic by addition of triethylamine and 2-chloro-4-fluoropyridine (0.02 g, 0.15 mmol) was added. The mixture was heated to 120° C. for 3 hours after which time it was diluted with ethyl acetate, washed with water, brine, dried with sodium sulfate, filtered and the solvent evaporated under reduced pressure. The residue was purified by column chromatography on silica gel using n-heptane/ethyl acetate (v/v 7:3 to 1:7) as eluent. The title compound was obtained as an off-white solid (0.05 g, 33%).

MS ISP (m/e): 481.2 [(M+H)⁺].

$^1$H NMR (CDCl$_3$, 400 MHz): δ (ppm)=8.11 (s, 1H), 8.00 (d, 1H), 7.97-7.91 (m, 1H), 7.71-7.67 (m, 1H), 7.34 (s, 1H), 7.23-7.16 (m, 1H), 6.57 (d, 1H), 6.48 (dd, 1H), 4.37-4.26 (m, 3H), 2.18-2.11 (m, 4H), 2.05-2.00 (m, 2H), 1.61 (t, 2H).

EXAMPLE 2

[(rac)-3-exo-8-(3-Methyl-[1,2,4]thiadiazol-5-yl)-8-aza-bicyclo[3.2.1]oct-3-yl]-(4-phenyl-4,5,6,7-tetrahydro-benzothiazol-2-yl)-amine

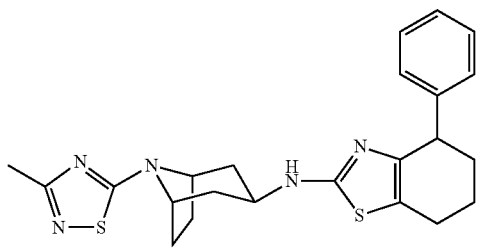 [SMILES: Cc1nsc(N2C3CCC2CC(Nc2nc4c(s2)CCCC4c2ccccc2)C3)n1]

a) 3-(4-Phenyl-4,5,6,7-tetrahydro-benzothiazol-2-ylamino)-(rac)-3-exo-8-aza-bicyclo[3.2.1]octane-8-carboxylic acid tert-butyl ester To a solution of 4-phenyl-4,5,6,7-tetrahydro-benzothiazol-2-ylamine (46 mg, 0.2 mmol) in dichloroethane (0.6 mL) was added at room temperature under stirring BOC-nortropinone (64 mg, 0.28 mmol) and tetraisopropyl-orthotitanat (178 µL, 0.6 mmol). The reaction was stirred over night at 90° C. in a sealed tube under nitrogen. At room temperature ethanol (0.6 mL) and sodium borohydride (15 mg, 0.4 mmol) were added and the reaction was stirred at 85° C. for 4 hours and 30 minutes. Water was added, the reaction was stirred for 30 minutes and the precipitate was filtered off and washed with ethanol. The filtrate was concentrated under reduced pressure. Water was added and the reaction was extracted twice with ethyl acetate. The combined organic layers were washed with concentrated aqueous sodium chloride solution, dried over sodium sulfate, filtered and concentrated under reduced pressure. The residue was purified by column chromatography on silica gel using a gradient from CH$_2$Cl$_2$ to CH$_2$Cl$_2$/MeOH 19:1 (v/v) as eluent to yield the title compound as a light brown solid (73 mg, 83%).

MS ISP (m/e): 440.3 (100) [(M+H)⁺].

b) ((rac)-3-exo-8-Aza-bicyclo[3.2.1]oct-3-yl)-(4-phenyl-4,5,6,7-tetrahydro-benzothiazol-2-yl)-amine hydrochloride To a solution of 3-(4-phenyl-4,5,6,7-tetrahydro-benzothiazol-2-ylamino)-(rac)-3-exo-8-aza-bicyclo[3.2.1]octane-8-carboxylic acid tert-butyl ester (93 mg, 0.21 mmol) in methylene chloride (5 mL) was added 2 M hydrogen chloride solution in diethyl ether (1.1 mL). The reaction was stirred at room temperature overnight. The solvent was removed under reduced pressure and the residue was treated with diethyl ether and evaporated. The title compound was obtained as a light brown solid (76 mg, 96%).

MS ISP (m/e): 340.2 (100) [(M+H)⁺], 231.2 (34).

c) [(rac)-3-exo-8-(3-Methyl-[1,2,4]thiadiazol-5-yl)-8-aza-bicyclo[3.2.1]oct-3-yl]-(4-phenyl-4,5,6,7-tetrahydro-benzothiazol-2-yl)-amine Palladium (II) acetate (3.3 mg, 0.015 mmol) and 2-(dicyclohexylphosphino)biphenyl (11 mg, 0.03 mmol) were stirred under nitrogen at room temperature in dioxane (1.7 mL) for 10 minutes. Sodium tert.-butylat (27 mg, 0.28 mmol), ((rac)-3-exo-8-aza-bicyclo[3.2.1]oct-3-yl)-(4-phenyl-4,5,6,7-tetrahydro-benzothiazol-2-yl)-amine hydrochloride (70 mg, 0.19 mmol), N,N-diisopropylethylamine (63 µL, 0.37 mmol) and 5-chloro-3-methyl-[1,2,4]thiadiazole (28 mg; 0.21 mmol) were added and the reaction was heated to 200° C. for 30 minutes in a microwave oven. The reaction was diluted with water and extracted twice with ethyl acetate. The combined organic layers were washed with water, dried over sodium sulfate, filtered and concentrated under reduced pressure. The residue was purified by column chromatography on silica gel using a gradient from CH$_2$Cl$_2$ to CH$_2$Cl$_2$/MeOH 19:1 (v/v) as eluent. The title compound was obtained as a light yellow solid (48 mg, 59%).

MS ISP (m/e): 438.2 (100) [(M+H)⁺].

$^1$H NMR (CDCl$_3$, 300 MHz): δ (ppm)=7.28 (d, 1H), 7.18 (t, 2H), 7.11 (t, 1H), 4.70 (m, 0.5H), 4.51 (m, 0.5H), 4.21 (m, 1.5H), 4.00 (m, 1H), 3.60 (m, 0.5H), 2.72 (m, 2H), 2.47 (s, 1.5H), 2.42 (s, 1.5H), 2.32 (m, 1H), 2.15 (m, 3H), 2.18 (m, 5H), 1.65 (m, 3H).

EXAMPLE 3

2-{6-(4-Chloro-benzyl)-2-[(rac)-3-endo-8-(3-methyl-[1,2,4]thiadiazol-5-yl)-8-aza-bicyclo[3.2.1]oct-3-ylamino]-pyrimidin-4-yl}-propan-2-ol

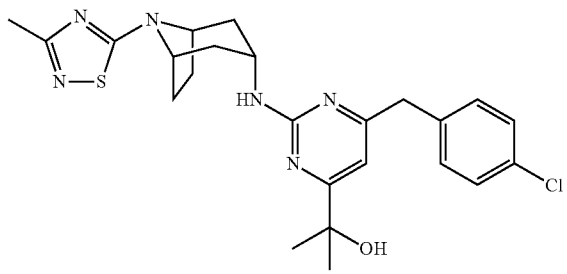 [SMILES: Cc1nsc(N2C3CCC2CC(Nc2nc(Cc4ccc(Cl)cc4)cc(C(C)(C)O)n2)C3)n1]

a) (rac)-3-[(Z)-Hydroxyimino]-8-aza-bicyclo[3.2.1]octane-8-carboxylic acid tert-butyl ester To a solution of Boc-nortropinone (1.13 g, 5 mmol) in ethanol (5 mL) was added under stirring hydroxylamine hydrochloride (0.695 g, 10 mmol) in water (5 mL). Sodium bicarbonate (0.84 g, 10 mmol) was added portion wise and the reaction was refluxed for 45 minutes under nitrogen and stirred at room temperature overnight. The solvent was evaporated under reduced pressure. Water was added and the reaction was extracted twice with ethyl acetate. The combined organic layers were dried over sodium sulfate, filtered and the solvent was evaporated under reduced pressure to yield the title compound as a brown oil (1.28 g, 100%).

b) (rac)-3-endo-3-Amino-8-aza-bicyclo[3.2.1]octane-8-carboxylic acid tert-butyl ester A solution of (rac)-3-[(Z)-hydroxyimino]-8-aza-bicyclo[3.2.1]octane-8-carboxylic acid tert-butyl ester (635 mg, 2.64 mmol) in ethanol (4 mL) and acetic acid (1 mL) was hydrogenated under an atmosphere of hydrogen over night at room temperature in the presence of $PtO_2$ (42 mg, 6.6 weight %). Another portion of $PtO_2$ (42 mg) was added and the reaction was further hydrogenated overnight. The catalyst was filtered off, washed with ethanol. The filtrate was concentrated under reduced pressure and the residue was purified by column chromatography on silica gel using $CH_2Cl_2/MeOH/NH_3$ 19:1:0.1 (v/v/v) as eluent to yield the title compound as a yellow solid (622 mg, 100%).

MS ISP (m/e): 227.3 (100) [(M+H)$^+$].

c) (rac)-(3-endo)-3-[4-(4-Chloro-benzyl)-6-(1-hydroxy-1-methyl-ethyl)-pyrimidin-2-ylamino]-8-aza-bicyclo[3.2.1]octane-8-carboxylic acid tert-butyl ester A solution of (rac)-3-endo-3-amino-8-aza-bicyclo[3.2.1]octane-8-carboxylic acid tert-butyl ester (189 mg, 0.837 mmol), 2-[2-chloro-6-(4-chloro-benzyl)-pyrimidin-4-yl]-propan-2-ol (342 mg, 0.92 mmol) and N,N-diisopropylethylamine (214 µL, 1.26 mmol) in dioxane (2 mL) was heated at 150° C. in a microwave oven for 1 hour. The reaction was diluted with water and extracted twice with ethyl acetate. The combined organic layers were washed with saturated aqueous sodium chloride solution, dried over sodium sulfate, filtered and concentrated under reduced pressure. The residue was purified by column chromatography on silica gel using a gradient from $CH_2Cl_2$ to $CH_2Cl_2$:MeOH 19:1 (v/v) as eluent. The title compound was obtained as a yellow oil (86 mg, 21%).

MS ISP (m/e): 487.4 (100) [(M+H)$^+$].

d) 2-[2-[(rac)-(3-endo)-(8-Aza-bicyclo[3.2.1]oct-3-yl)amino]-6-(4-chloro-benzyl)-pyrimidin-4-yl]-propan-2-ol hydrochloride To a solution of (rac)-3-endo-3-[4-(4-chloro-benzyl)-6-(1-hydroxy-1-methyl-ethyl)-pyrimidin-2-ylamino]-8-aza-bicyclo[3.2.1]octane-8-carboxylic acid tert-butyl ester (86 mg, 0.177 mmol) in methylene chloride (2 mL) was added at room temperature under stirring a 2 M hydrogen chloride solution in diethyl ether (0.9 mL) and was stirred at room temperature overnight. The solvent was removed under reduced pressure and trifluoroacetic acid (2 mL) was added. The solvent was removed under reduced pressure to yield the title compound as a brown gum (95 mg, 127%)

MS ISP (m/e): 387.4 (100) [(M+H)$^+$].

e) 2-{6-(4-Chloro-benzyl)-2-[(rac)-3-endo-8-(3-methyl-[1,2,4]thiadiazol-5-yl)-8-aza-bicyclo[3.2.1]oct-3-ylamino]-pyrimidin-4-yl}-propan-2-ol Palladium (II) acetate (3.8 mg, 0.017 mmol) and 2-(dicyclohexylphosphino)biphenyl (12 mg, 0.034 mmol) were stirred under nitrogen at room temperature in dioxane (1 mL) for 10 minutes. Sodium tert.-butylat (32 mg, 0.32 mmol), 2-[2-[(rac)-3-endo-(8-aza-bicyclo[3.2.1]oct-3-yl)amino]-6-(4-chloro-benzyl)-pyrimidin-4-yl]-propan-2-ol hydrochloride (90 mg, 0.213 mmol), N,N-diisopropylethylamine (72.3 µl, 0.425 mmol) in dioxane (2 mL) and 5-chloro-3-methyl-[1,2,4]-thiadiazole (32 mg; 0.234 mmol) were added and the reaction was heated to 150° C. for 1 hour in a microwave oven. The reaction was diluted with water and extracted twice with ethyl acetate. The combined organic layers were washed with saturated aqueous sodium chloride solution, dried over sodium sulfate, filtered and concentrated under reduced pressure. The residue was purified by column chromatography on silica gel using a gradient from $CH_2Cl_2$ to $CH_2Cl_2$:MeOH 19:1 (v/v) as eluent. The title compound was obtained as a light brown gum (55 mg, 48%).

MS ISP (m/e): 485.4/487.4 (100/33) [(M+H)$^+$], 467.3/469.3 (38/16).

$^1$H NMR (CDCl$_3$, 300 MHz): δ (ppm)=7.28 (d, 2H), 7.19 (d, 2H), 6.43 (s, 1H), 4.94 (br d, 1H), 4.22 (m, 2H), 4.19 (m, 1H), 3.85 (s, 2H), 3.70 (s, 1H), 2.45 (m, 2H), 2.44 (s, 3H), 2.19 (m, 4H), 1.92 (d, 2H), 1.41 (s, 6H).

EXAMPLE 4

[8-(3,4-Difluoro-phenyl)-[1,2,4]triazolo[1,5-a]pyridin-2-yl]-[(rac)-8-endo-3-(2-trifluoromethyl-pyridin-4-yl)-3-aza-bicyclo[3.2.1]oct-8-yl]-amine

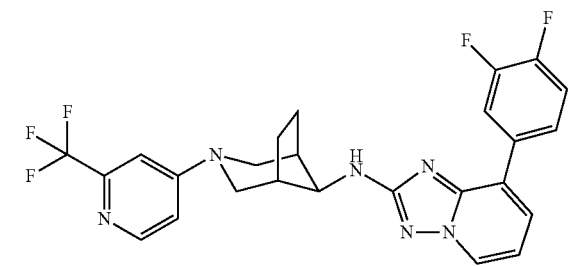 [SMILES: Fc1ccc(-c2cccn3nc(NC4C5CCC4CN(c4ccnc(C(F)(F)F)c4)C5)nc23)cc1F]

a) (rac)-8-endo-3-Benzyl-3-azabicyclo[3.2.1]octan-8-amine (rac)-3-Benzyl-3-azabicyclo[3.2.1]octan-8-one oxime (1.2 g, 5.1 mmol, WO2005/21536 A2) was dissolved in methanol (20 mL), a generous spatula of Raney nickel was added and the mixture stirred under an atmosphere of hydrogen for 1 hour after which time it was filtered through Hyflo® and concentrated. The residue was purified by column chromatography on silica gel using a gradient from $CH_2Cl_2$: MeOH (v/v 9:1-7:3) as eluent. The title compound was obtained as a waxy solid (0.3 g, 26%) as well as the earlier eluting exo-isomer (0.4 g, 36%).

MS ISP (m/e): 217.2 [(M+H)$^+$].

$^1$H NMR (CDCl$_3$, 400 MHz): δ (ppm)=7.32-7.21 (m, 5H), 3.46 (s, 2H), 2.88 (s, 1H), 2.67 (dd, 2H), 2.11 (d, 2H), 1.97 (brs, 2H), 1.81-1.74 (m, 4H).

b) N-(3-Bromo-pyridin-2-yl)-N'-ethoxycarbonyl-thiourea

3-Bromopyridin-2-amine (30 g, 168 mmol) and ethoxycarbonyl isothiocyanate (24.8 g, 21.3 mL, 185 mmol) were dissolved in dioxane (300 mL) and stirred at room temperature. After 4 hours further ethoxycarbonyl isothiocyanate (1 mL, 8.4 mmol) was added. After 1 hour the solvent was evaporated and the residue dried in high vacuum for 12 hours. The title compound was obtained as a light yellow solid (51.2 g, 100%) and was used crude for the next step.

MS ISP (m/e): 304.0/305.9 (100/73) [(M+H)$^+$].

¹H NMR (CDCl₃, 300 MHz): δ=(ppm)=8.41 (m, 1H) 7.99-7.96 (m, 1H), 7.11-7.07 (m, 1H), 4.32 (q, 2H), 1.36 (t, 3H).

c) 8-Bromo-[1,2,4]triazolo[1,5-a]pyridin-2-amine

Hydroxylamine (58.5 g, 842 mmol) and N,N-diisopropylethylamine (65.3 g, 86.3 mL, 505 mmol) were dissolved in methanol (200 mL) and ethanol (200 mL). N-(3-Bromo-pyridin-2-yl)-N'-ethoxycarbonyl-thiourea (51.2 g, 168 mmol) was added and the reaction mixture was stirred at room temperature for 1 hour and then at 60° C. for 3 hours. The white precipitate was filtered off and triturated with water for 25 minutes, filtered and triturated two times with diethyl ether. The solid was dried by co-evaporation with toluene and dried in vacuum. The title compound was obtained as a white solid (27.9 g, 78%).

MS ISP (m/e): 213.0/215.1 (86/95) [(M+H)⁺].

¹H NMR (CDCl₃, 300 MHz): δ (ppm)=8.28 (dd, 1H) 7.62 (dd, 1H), 6.73 (t, 1H), 4.66 (bs, 2H).

d) 8-(3,4-Difluoro-phenyl)-[1,2,4]triazolo[1,5-a]pyridin-2-ylamine

A suspension of 8-bromo-[1,2,4]triazolo[1,5-a]pyridin-2-amine (5.33 g, 25 mmol), 3,4-difluorophenylboronic acid (5.92 g, 37.5 mmol) and 2M aqueous sodium carbonate solution (62.5 mL, 125 mmol) in 1,4-dioxane (250 mL) was treated with 1,1'-bis(diphenylphosphino)ferrocene-palladium(II)dichloride dichloromethane complex (1.02 g, 1.25 mmol) at room temperature and then stirred for 18 hours at 110° C. The reaction was cooled to room temperature and separated between water (312 mL) and ethyl acetate (500 mL). The aqueous layer was extracted with further ethyl acetate (500 mL). The organic layers were washed with saturated aqueous sodium chloride solution (300 mL), combined, dried over sodium sulfate, filtered off and evaporated. The brown solid was trituration with diethyl ether (130 mL) and dichloromethane (25 mL) to yield the title compound as a light brown solid (6.33 g, 97%). MS ISP (m/e): 247.2 (100) [(M+H)⁺].

e) 2-Bromo-8-(3,4-difluorophenyl)-[1,2,4]triazolo[1,5-a]pyridine

A solution of copper(II) bromide (5.86 g, 26.3 mmol) and tert-butylnitrite (3.01 g, 3.48 mL, 26.3 mmol) in acetonitrile (93 mL) was added 8-(3,4-difluorophenyl)-[1,2,4]triazolo[1,5-a]pyridin-2-amine (4.30 g, 17.5 mmol) in portions at 60° C. The reaction was stirred for 2 hours at 75° C., cooled to room temperature and quenched with 1M aqueous hydrogen chloride solution (186 mL). The mixture was extracted with dichloromethane (186 mL) three times. The organic layers were combined, dried over sodium sulfate, filtered off and evaporated. Flash chromatography over silica gel (120 g) with dichloromethane gave the title compound as a light yellow solid (4.30 g, 79%).

MS ISP (m/e): 310.2/312.0 (100/100) [(M+H)⁺].

f) N-((rac)-8-endo-3-Benzyl-3-azabicyclo[3.2.1]oct-8-yl)-8-(3,4-difluorophenyl)-[1,2,4]triazolo[1,5-a]pyridin-2-amine A solution 2-bromo-8-(3,4-difluorophenyl)-[1,2,4]triazolo[1,5-a]pyridine (85 mg, 0.27 mmol), (rac)-8-endo-3-benzyl-3-azabicyclo[3.2.1]octan-8-amine (50 mg, 0.23 mmol) and sodium phenoxide (40 mg, 0.35 mmol) in dry 1,4-dioxane (1 mL) in a sealed tube was purged with argon for 10 minutes. Pd₂(dba)₃.CHCl₃ (19 mg, 0.02 mmol) and xanthphos (21 mg, 0.04 mmol) were added to the solution and degassing continued for another 5 minutes before the reaction mixture was heated to 130° C. for 0.5 hours. The reaction was diluted with dichloromethane, washed with 1M aqueous sodium carbonate solution, the organic phase was dried over sodium sulfate, the solvent was evaporated The residue was purified by column chromatography on silica gel using n-heptane/ethyl acetate (v/v 8:2 to 1:1) as eluent. The title compound was obtained as a light yellow solid (88 mg, 85%).

MS ISP (m/e): 446.2 [(M+H)⁺].

¹H NMR (CDCl₃, 400 MHz): δ (ppm)=8.35 (d, 1H), 7.90 (dd, 1H), 7.70-7.65 (m, 1H), 7.46 (d, 1H), 7.33-7.24 (m, 6H), 6.86 (t, 1H), 4.48 (d, 1H), 3.68 (d, 1H), 3.53 (s, 2H), 2.74 (dd, 2H), 2.33-2.30 (m, 4H), 1.86-1.62 (m 4H).

g) [8-(3,4-Difluoro-phenyl)-[1,2,4]triazolo[1,5-a]pyridin-2-yl]-[(rac)-8-endo-3-(2-trifluoromethyl-pyridin-4-yl)-3-aza-bicyclo[3.2.1]oct-8-yl]-amine To N-((rac)-8-endo-3-benzyl-3-azabicyclo[3.2.1]octan-8-yl)-8-(3,4-difluorophenyl)-[1,2,4]triazolo[1,5-a]pyridin-2-amine (0.09 g, 0.2 mmol) in methanol (5 mL) was added a generous spatula of 10% palladium on charcoal, followed by a few drops of 25% aqueous hydrochloric acid and the mixture was stirred under an atmosphere of hydrogen for two days. The reaction was then filtered over Hyflo® and concentrated to dryness. The residue was redissolved in dimethylacetamide (1 mL), triethylamine was added until the pH was basic followed by addition of 4-iodo-2-(trifluoromethyl)pyridine (0.05 g, 0.2 mmol) and the mixture was heated to 135° C. for 16 hours. The reaction was then diluted with ethyl acetate, washed repeatedly with water, then brine, dried over sodium sulfate and concentrated. The residue was purified by column chromatography on silica gel using n-heptane/ethyl acetate (v/v 1:1) as eluent. The title compound was obtained as a light yellow solid (8.4 mg, 9%).

MS ISP (m/e): 501.2 [(M+H)⁺].

¹H NMR (CDCl₃, 400 MHz): δ (ppm)=8.35 (d, 1H), 8.40 (d, 1H), 7.90 (dd, 1H), 7.71-7.68 (m, 1H), 7.46 (d, 1H), 7.31-7.24 (m, 1H), 7.00 (d, 1H), 6.92 (t, 1H), 6.73 (dd, 1H), 4.57 (d, 1H), 3.98 (d, 1H), 3.72 (dd, 2H), 3.23 (d, 2H), 2.65 (s, 2H), 2.04-1.98 (m, 2H), 1.68-1.62 (m 2H).

EXAMPLE 5

[(rac)-8-endo-3-(6-Methyl-pyrimidin-4-yl)-3-azabicyclo[3.2.1]oct-8-yl]-[8-(2,3,4-trifluoro-phenyl)-[1,2,4]triazolo[1,5-a]pyridin-2-yl]-amine

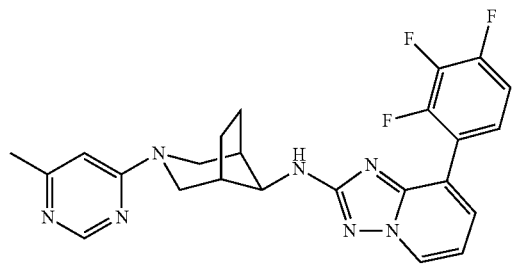 [SMILES: Cc1cc(N2CC3CCC(C2)C3Nc2nc3c(-c4ccc(F)c(F)c4F)cccn3n2)ncn1]

a) 2-Bromo-8-(2,3,4-trifluorophenyl)-[1,2,4]triazolo[1,5-a]pyridine

The title compound, a white solid, was prepared in analogy to example 4 step d to e from 8-bromo-[1,2,4]triazolo[1,5-a]pyridin-2-amine and 2,3,4-trifluorophenylboronic acid.

b) N-((rac)-8-endo-3-Benzyl-3-azabicyclo[3.2.1]octan-8-yl)-8-(2,3,4-trifluorophenyl)-[1,2,4]triazolo[1,5-a]pyridin-2-amine The title compound, a light brown foam, was prepared in analogy to example 4f from (rac)-8-endo-3-benzyl-3-azabicyclo[3.2.1]octan-8-amine and 2-bromo-8-(2,3,4-trifluorophenyl)-[1,2,4]triazolo[1,5-a]pyridine.

MS ISP (m/e): 464.2 [(M+H)$^+$].

$^1$H NMR (CDCl$_3$, 400 MHz): δ (ppm)=8.35 (d, 1H), 7.69-7.64 (m, 1H), 7.58-7.52 (m, 1H), 7.44 (dt, 1H), 7.33-7.24 (m, 5H), 6.86 (t, 1H), 4.48 (d, 1H), 3.66 (d, 1H), 3.52 (s, 2H), 2.74 (dd, 2H), 2.33-2.30 (m, 4H), 1.83-1.74 (m 4H).

c) [(rac-8-endo-3-(6-Methyl-pyrimidin-4-yl)-3-azabicyclo[3.2.1]oct-8-yl]-[8-(2,3,4-trifluoro-phenyl)-[1,2,4]triazolo[1,5-a]pyridin-2-yl]-amine The title compound, a light brown foam, was prepared in analogy to example 4g from N-((rac)-8-endo-3-benzyl-3-azabicyclo[3.2.1]octan-8-yl)-8-(2,3,4-trifluorophenyl)-[1,2,4]triazolo[1,5-a]pyridin-2-amine and 4-chloro-6-methylpyrimidine.

MS ISP (m/e): 466.2 [(M+H)$^+$].

$^1$H NMR (CDCl$_3$, 400 MHz): δ (ppm)=8.51 (s, 1H), 8.37 (d, 1H), 7.55-7.49 (m, 2H), 7.11-7.05 (m, 1H), 7.31-7.24 (m, 1H), 6.92 (t, 1H), 6.36 (s, 1H), 4.70 (d, 1H), 3.96 (d, 1H), 3.38 (t, 1H), 3.15 (d, 2H), 2.85 (s, 2H), 2.55 (brs, 2H), 2.40-2.35 (m, 4H), 1.88-1.85 (m 2H).

EXAMPLE 6

[(rac)-8-endo-3-(3-Methyl-[1,2,4]thiadiazol-5-yl)-3-aza-bicyclo[3.2.1]oct-8-yl]-[8-(2-chloro-4-fluorophenyl)-6-methyl-[1,2,4]triazolo[1,5-a]pyridin-2-yl]-amine

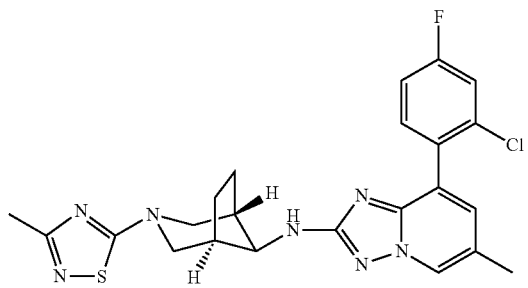 [SMILES: Cc1cc(-c2ccc(F)cc2Cl)c2nc(NC3[C@@H]4CC[C@H]3CN(c3nc(C)ns3)C4)nn2c1]

a) [(rac)-8-endo-Benzyl-3-aza-bicyclo[3.2.1]oct-8-yl]-carbamic acid tert-butyl ester To a solution of (rac)-8-endo-3-benzyl-3-azabicyclo[3.2.1]octan-8-amine (3.9 g, 17.9 mmol) in dichloromethane (40 mL) was added Boc-anhydride (6.19 mL, 26.9 mmol), and the reaction mixture was stirred at 25° C. for 2 hours. Removal of solvent under reduced pressure followed by purification of the resulting crude material by column chromatography over normal silica gel (0-10% EtOAc/hexane) yielded the title compound as a white solid (4.5 g, 79%).

$^1$H NMR (DMSO-d$_6$, 400 MHz): δ (ppm)=7.33-7.27 (m, 4H), 7.23-7.21 (m, 1H), 6.60 (br s, 1H, NH), 3.44 (s, 2H), 3.25 (m, 1H), 2.58 (dm, 2H), 2.07 (br d, 2H), 2.03 (br s, 1H), 1.70 (br m, 2H), 1.55 (br m, 2H), 1.37 (s, 9H).

b) [(rac)-8-endo-3-Aza-bicyclo[3.2.1]oct-8-yl]-carbamic acid tert-butyl ester To a solution of [(rac)-8-endo-benzyl-3-aza-bicyclo[3.2.1]oct-8-yl]-carbamic acid tert-butyl ester (4.5 g, 14.2 mmol) in methanol (60 mL) was added Pd/C (10%; 750 mg), and the reaction mixture was stirred under hydrogen balloon atmosphere at 25° C. for 3 hours. The reaction mixture was filtered through a bed of celite, and the filtrate was evaporated off in vacuo to yield the title compound as a white solid (3.1 g, 96%).

MS ISP (m/e): 227.2 (95) [(M+H)$^+$], 171.2 (100).

$^1$H NMR (DMSO-d$_6$, 400 MHz): δ (ppm)=6.52 (br s, 1H, NH), 2.55 (m, 4H), 1.91 (br s, 2H), 1.68 (m, 2H), 1.42 (m, 2H), 1.37 (s, 9H).

c) [(rac)-8-endo-3-(3-Methyl-[1,2,4]thiadiazol-5-yl)-3-aza-bicyclo[3.2.1]oct-8-yl]-carbamic acid tert-butyl ester To a solution of [(rac)-8-endo-3-aza-bicyclo[3.2.1]oct-8-yl]-carbamic acid tert-butyl ester (3.5 g, 15.4 mmol) in ethanol (40 mL) in a sealed tube were added 5-chloro-3-methyl-[1,2,4]thiadiazole (1.73 mL, 18.5 mmol) and triethyl amine (3.26 mL, 23.2 mmol). The reaction mixture was stirred at 100° C. for 12 hours. The solvent was removed in vacuo. The resulting crude material was purified by column chromatography over normal silica gel (0-15% EtOAc/hexane) to yield the title compound as a white solid (3.9 g, 91%).

MS ISP (m/e): 325.2 (95) [(M+H)$^+$], 269.0 (100).

d) (rac)-8-endo-3-(3-Methyl-[1,2,4]thiadiazol-5-yl)-3-aza-bicyclo[3.2.1]octan-8-amine To a solution of [(rac)-8-endo-3-(3-methyl-[1,2,4]thiadiazol-5-yl)-3-aza-bicyclo[3.2.1]oct-8-yl]-carbamic acid tert-butyl ester (700 mg, 2.16 mmol) in dichloromethane (15 mL) was added trifluoroacetic acid (2.5 mL), and the reaction mixture was stirred at 25° C. for 2 hours. Volatilities were removed in vacuo. The resultant residue was neutralized with saturated aqueous sodium bicarbonate solution, and extracted with dichloromethane (2×30 mL). The combined organic layer was dried over anhydrous sodium sulfate, filtered, and the solvent was evaporated off in vacuo to yield the title compound as a white solid (480 mg, 96%).

MS ISP (m/e): 225.0 (100) [(M+H)$^+$].

e) [(rac)-8-endo-3-(3-Methyl-[1,2,4]thiadiazol-5-yl)-3-aza-bicyclo[3.2.1]oct-8-yl]-[8-(2-chloro-4-fluorophenyl)-6-methyl-[1,2,4]triazolo[1,5-a]pyridin-2-yl]-amine To a solution of 2-bromo-8-(2-chloro-4-fluorophenyl)-6-methyl-[1,2,4]triazolo[1,5-a]pyridine (CAS 1329673-52-0; US 20110201605) (30 mg, 0.088 mmol) in dry 1,4-dioxane (2 mL) were added (rac)-8-endo-3-(3-methyl-[1,2,4]thiadiazol-5-yl)-3-aza-bicyclo[3.2.1]octan-8-amine (29.6 mg, 0.13 mmol) and sodium phenoxide (15.3 mg, 0.132 mmol). The mixture was purged with argon for 10 minutes. To this mixture were then added Pd$_2$(dba)$_3$·CHCl$_3$ (7.3 mg, 0.007 mmol) and xantphos (8.16 mg, 0.014 mmol). The reaction mixture was purged again with argon for 10 minutes. The reaction mixture was heated to 130° C. for 0.5 hours in the microwave. It was diluted with EtOAc (10 mL), and washed with water (5 mL). The organic layer was dried over anhydrous sodium sulfate, filtered, and the solvent was evaporated off in vacuo. The resulting crude material was purified by preparative HPLC to yield the title compound as an off-white solid (8.8 mg, 21%).

MS ISP (m/e): 484.2/486.2 (100/35) [(M+H)$^+$].

$^1$H NMR (DMSO-d$_6$, 400 MHz): δ (ppm)=8.57 (br s, 1H, NH), 7.59 (m, 2H), 7.33 (m, 2H), 6.70 (d, 1H), 4.02 (q, 1H), 3.75 (m, 1H), 3.55 (br m, 1H), 3.36 (d, 2H), 2.33 (s, 3H), 2.27 (s, 3H), 1.91 (m, 2H), 1.39 (br d, 2H).

EXAMPLE 7

[(rac)-8-endo-3-(3-Methyl-[1,2,4]thiadiazol-5-yl)-3-aza-bicyclo[3.2.1]oct-8-yl]-[8-(2-chloro-4-fluoro-phenyl)-6-fluoro-[1,2,4]triazolo[1,5-a]pyridin-2-yl]-amine

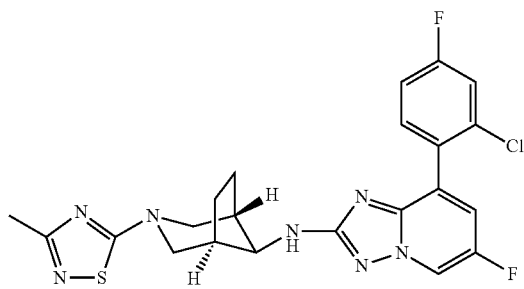 [SMILES: Cc1nsc(N2C[C@H]3CC[C@@H](C2)C3Nc2nc3c(-c4ccc(F)cc4Cl)cc(F)cn3n2)n1]

a) 2-Bromo-8-(2-chloro-4-fluoro-phenyl)-6-fluoro-[1,2,4]triazolo[1,5-a]pyridine

To a solution of copper(II) bromide (60 mg, 0.268 mmol) and tert-butyl nitrite (27.8 mg, 0.268 mmol) in acetonitrile (2 mL) at 60° C. was added 8-(2-chloro-4-fluoro-phenyl)-6-fluoro-[1,2,4]triazolo[1,5-a]pyridin-2-yl-amine (CAS 1319068-45-5; WO2011092272) (50 mg, 0.179 mmol) in one portion, and the reaction was stirred for 2 hours at 75° C. The reaction mixture was cooled to 25° C., and quenched with aqueous HCl solution (1M, 5 mL). The reaction mixture was diluted with water (5 mL), and extracted with EtOAc (2×10 mL). The combined organic layer was dried over anhydrous sodium sulfate, filtered, and evaporated off under reduced pressure to yield the title compound (55 mg, crude) as brown solid which was used in the next step without any further purification. MS ISP (m/e): 344.2/346.2 (98/100) [(M+H)$^+$].

b) [(rac)-8-endo-3-(3-Methyl-[1,2,4]thiadiazol-5-yl)-3-aza-bicyclo[3.2.1]oct-8-yl]-[8-(2-chloro-4-fluoro-phenyl)-6-fluoro-[1,2,4]triazolo[1,5-a]pyridin-2-yl]-amine The title compound was prepared in analogy to example 6e from (rac)-8-endo-3-(3-methyl-[1,2,4]thiadiazol-5-yl)-3-aza-bicyclo[3.2.1]octan-8-amine (48.8 mg, 0.021 mmol) and 2-bromo-8-(2-chloro-4-fluoro-phenyl)-6-fluoro-[1,2,4]triazolo[1,5-a]pyridine (CAS 1319068-45-5; WO 2011092272) (50 mg, 0.14 mmol) as a white solid (11.3 mg, 16%).

MS ISP (m/e): 488.0/489.1 (100/35) [(M+H)$^+$].

$^1$H NMR (DMSO-d$_6$, 400 MHz): δ (ppm)=9.11 (q, 1H), 7.66-7.60 (m, 3H), 7.37 (t, 1H), 6.87 (d, 1H), 3.75 (d, 1H), 3.58 (br m, 2H), 3.35 (d, 2H), 2.45 (br s, 2H), 2.27 (s, 3H), 1.91 (m, 2H), 1.39 (br d, 2H).

EXAMPLE 8

[(rac)-8-endo-3-(3-Methyl-[1,2,4]thiadiazol-5-yl)-3-aza-bicyclo[3.2.1]oct-8-yl]-[8-(4-chloro-2-methoxy-phenyl)-[1,2,4]triazolo[1,5-a]pyridin-2-yl]-amine

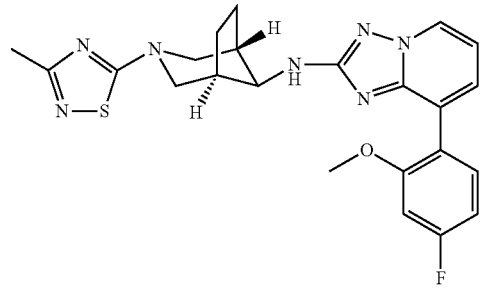 [SMILES: COc1cc(F)ccc1-c1cccn2nc(NC3[C@@H]4CC[C@H]3CN(c3nc(C)ns3)C4)nc12]

a) 2-Bromo-8-(4-fluoro-2-methoxyphenyl)-[1,2,4]triazolo[1,5-a]pyridine

The title compound, a white solid, was prepared in analogy to example 4 step d to e from 8-bromo-[1,2,4]triazolo[1,5-a]pyridin-2-amine and 4-fluoro-2-methoxyphenylboronic acid. MS ISP (m/e): 322.2/324.2 (100/100) [(M+H)$^+$].

b) [(Rac)-8-endo-3-(3-Methyl-[1,2,4]thiadiazol-5-yl)-3-aza-bicyclo[3.2.1]oct-8-yl]-[8-(4-chloro-2-methoxy-phenyl)-[1,2,4]triazolo[1,5-a]pyridin-2-yl]-amine The title compound was prepared in analogy to example 6e from (rac)-8-endo-3-(3-methyl-[1,2,4]thiadiazol-5-yl)-3-aza-bicyclo[3.2.1]octan-8-amine (52.1 mg, 0.23 mmol) and 2-bromo-8-(4-fluoro-2-methoxy-phenyl)-[1,2,4]triazolo[1,5-a]pyridine (50 mg, 0.14 mmol) as an off-white solid (13.8 mg, 19%).

MS ISP (m/e): 466.0 (100) [(M+H)$^+$].

$^1$H NMR (DMSO-d$_6$, 400 MHz): δ (ppm)=8.61 (br s, 1H, NH), 7.57 (t, 1H), 7.43 (d, 1H), 7.04 (dd, 1H), 6.92 (t, 1H), 6.88 (dt, 1H), 6.73 (d, 1H), 3.76 (s, 3H), 3.77 (m, 1H), 3.58 (br m, 2H), 3.37 (d, 2H), 2.27 (s, 3H), 1.92 (m, 2H), 1.40 (br d, 2H).

EXAMPLE 9

[(rac)-8-endo-3-(3-Methyl-[1,2,4]thiadiazol-5-yl)-3-aza-bicyclo[3.2.1]oct-8-yl]-[8-(3-cyano-4-fluoro-phenyl)-[1,2,4]triazolo[1,5-a]pyridin-2-yl]-amine

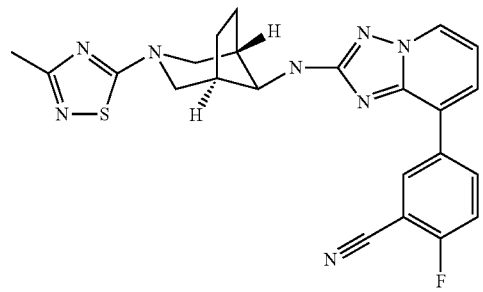 [SMILES: Cc1nsc(N2C[C@H]3CC[C@@H](C2)C3Nc2nc3c(-c4ccc(F)c(C#N)c4)cccn3n2)n1]

a) 5-(2-Bromo-[1,2,4]triazolo[1,5-a]pyridine-8-yl)-2-fluorobenzonitrile

The title compound, a white solid, was prepared in analogy to example 4 step d to e from 8-bromo-[1,2,4]triazolo[1,5-a]pyridin-2-amine and 4-fluoro-3-cyanophenylboronic acid.
MS ISP (m/e): 317.0/319.0 (98/100) [(M+H)$^+$].

b) [(rac)-8-endo-3-(3-Methyl-[1,2,4]thiadiazol-5-yl)-3-aza-bicyclo[3.2.1]oct-8-yl]-[8-(3-cyano-4-fluoro-phenyl)-[1,2,4]triazolo[1,5-a]pyridin-2-yl]-amine The title compound was prepared in analogy to example 6e from (rac)-8-endo-3-(3-methyl-[1,2,4]thiadiazol-5-yl)-3-aza-bicyclo[3.2.1]octan-8-amine (39.2 mg, 0.17 mmol) and 5-(2-bromo-[1,2,4]triazolo[1,5-a]pyridine-8-yl)-2-fluoro-benzonitrile (37 mg, 0.11 mmol) as an off-white solid (14.6 mg, 27%). MS ISP (m/e): 461.4 (100) [(M+H)$^+$].

EXAMPLE 10

[(rac)-8-endo-3-(3-Methyl-[1,2,4]thiadiazol-5-yl)-3-aza-bicyclo[3.2.1]oct-8-yl]-[8-(3,4-difluoro-phenyl)-6-trifluoromethly-[1,2,4]triazolo[1,5-a]pyridin-2-yl]-amine

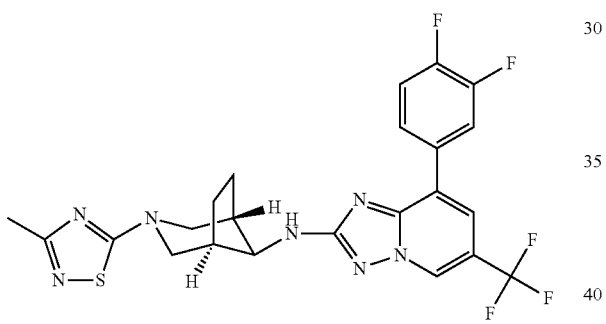

a) 2-Bromo-8-(3,4-difluoro-phenyl)-6-trifluoromethyl-[1,2,4]triazolo[1,5-a]pyridine The title compound, a brown solid, (57 mg, crude), was prepared in analogy to example 7a from 8-(3,4-difluoro-phenyl)-6-trifluoromethyl-[1,2,4]triazolo[1,5-a]pyridine-2-yl-amine (CAS 1319068-34-2, WO 2011092272) (50 mg, 0.159 mmol).
MS ISP (m/e): 378.0/380.1 (100/98) [(M+H)$^+$].

b) [(rac)-8-endo-3-(3-Methyl-[1,2,4]thiadiazol-5-yl)-3-aza-bicyclo[3.2.1]oct-8-yl]-[8-(3,4-difluoro-phenyl)-6-trifluoromethly-[1,2,4]triazolo[1,5-a]pyridin-2-yl]-amine The title compound was prepared in analogy to example 6e from (rac)-8-endo-3-(3-methyl-[1,2,4]thiadiazol-5-yl)-3-aza-bicyclo[3.2.1]octan-8-amine (44.4 mg, 0.19 mmol) and 2-bromo-8-(3,4-difluoro-phenyl)-6-trifluoro[1,2,4]triazolo[1,5-a]pyridine (CAS 1319068-34-2, WO2011092272) (50 mg, 0.13 mmol) as an off-white solid (22.0 mg, 14%).
MS ISP (m/e): 522.2 (100) [(M+H)$^+$].
$^1$H NMR (DMSO-d$_6$, 400 MHz): δ (ppm)=9.35 (br s, 1H, NH), 8.38 (dd, 1H), 8.12 (m, 1H), 8.08 (s, 1H), 7.59 (q, 1H), 7.27 (d, 1H), 3.84 (d, 1H), 3.59 (br m, 2H), 3.39 (d, 2H), 2.54 (br s, 2H), 2.28 (s, 3H), 1.98 (m, 2H), 1.44 (br d, 2H).

EXAMPLE 11

[(rac)-8-endo-3-(3-Methyl-[1,2,4]thiadiazol-5-yl)-3-aza-bicyclo[3.2.1]oct-8-yl]-[8-methoxy-[1,2,4]triazolo[1,5-a]pyridin-2-yl]-amine

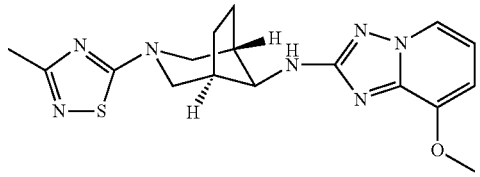

The title compound was prepared in analogy to example 6e from (rac)-8-endo-3-(3-methyl-[1,2,4]thiadiazol-5-yl)-3-aza-bicyclo[3.2.1]octan-8-amine (51.5 mg, 0.23 mmol) and 2-bromo-8-methoxyl-[1,2,4]triazolo[1,5-a]pyridine (CAS 1319067-40-7; WO 2011092272) (35 mg, 0.15 mmol) as a white solid (15.3 mg, 27%).
MS ISP (m/e): 372.2 (100) [(M+H)$^+$].
$^1$H NMR (DMSO-d$_6$, 400 MHz): δ (ppm)=8.21 (br d, 1H), 6.92 (d, 1H), 6.79 (t, 1H), 6.56 (d, 1H), 3.91 (s, 3H), 3.81 (d, 1H), 3.57 (br m, 2H), 3.38 (d, 2H), 3.23 (m, 1H), 2.27 (s, 3H), 1.94 (m, 2H), 1.41 (br d, 2H).

EXAMPLE 12

[(rac)-8-endo-3-(3-Methyl-[1,2,4]thiadiazol-5-yl)-3-aza-bicyclo[3.2.1]oct-8-yl]-[8-chloro-6-trifluoromethyl-[1,2,4]triazolo[1,5-a]pyridin-2-yl]-amine

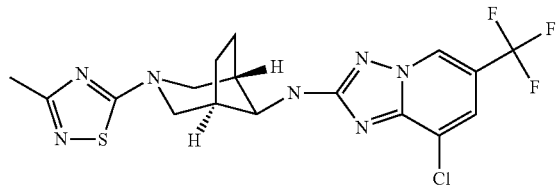 [SMILES: Cc1nsc(N2C[C@H]3CC[C@@H](C2)C3Nc2nc3c(Cl)cc(C(F)(F)F)cn3n2)n1]

a) 2-Bromo-8-chloro-6-trifluoromethyl[1,2,4]triazolo[1,5-a]pyridine

The title compound, a brown solid, (60 mg, crude), was prepared in analogy to example 7a from 8-chloro-6-trifluoromethyl-[1,2,4]triazolo[1,5-a]pyridine-2-yl-amine (CAS 1206640-61-0; WO2011092272) (50 mg, 0.212 mmol).
MS ISP (m/e): 300.2/302.0 (80/100) [(M+H)$^+$].

b) [(rac)-8-endo-3-(3-Methyl-[1,2,4]thiadiazol-5-yl)-3-aza-bicyclo[3.2.1]oct-8-yl]-[8-chloro-6-trifluoromethyl-[1,2,4]triazolo[1,5-a]pyridin-2-yl]-amine The title compound was prepared in analogy to example 6e from (r ac)-8-endo-3-(3-methyl-[1,2,4]thiadiazol-5-yl)-3-aza-bicyclo[3.2.1]octan-8-amine (56.0 mg, 0.25 mmol) and 2-bromo-8-chloro-6-trifluoromethyl-[1,2,4]triazolo[1,5-a]pyridine (CAS 1206640-61-0; WO2011092272) (50 mg, 0.167 mmol) as an off-white solid (8.7 mg, 12%). MS ISP (m/e): 444.2/445.2 (100/36) [(M+H)+].

EXAMPLE 13

[(rac)-8-endo-3-(3-Methyl-[1,2,4]thiadiazol-5-yl)-3-aza-bicyclo[3.2.1]oct-8-yl]-[5,6-dimethyl-[1,2,4]triazolo[1,5-a]pyridin-2-yl]-amine

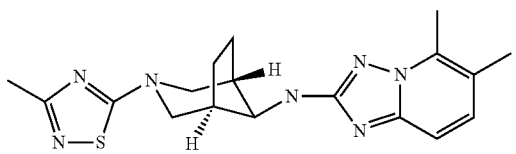

a) 2-Bromo-5,6-dimethyl-[1,2,4]triazolo-[1,5-a]pyridine

The title compound, a brown solid, (50 mg, crude), was prepared in analogy to example 7a from 5,6-dimethyl-[1,2,4]triazolo[1,5-a]pyridine-2-yl-amine (CAS 1319067-94-1; WO 2011092272) (40 mg, 0.24 mmol).
MS ISP (m/e): 226.2/228.0 (90/100) [(M+H)+].

b) [(rac)-8-endo-3-(3-Methyl-[1,2,4]thiadiazol-5-yl)-3-aza-bicyclo[3.2.1]oct-8-yl]-[5,6-dimethyl-[1,2,4]triazolo[1,5-a]pyridin-2-yl]-amine The title compound was prepared in analogy to example 6e from (rac)-8-endo-3-(3-methyl-[1,2,4]thiadiazol-5-yl)-3-aza-bicyclo[3.2.1]octan-8-amine (74.3 mg, 0.33 mmol) and 2-bromo-5,6-dimethyl-[1,2,4]triazolo[1,5-a]pyridine (CAS 1319067-94-1; WO2011092272) (50 mg, 0.22 mmol) as a white solid (11.9 mg, 15%).
MS ISP (m/e): 369.8 (100) [(M+H)+].

EXAMPLE 14

[(rac)-8-endo-3-(3-Methyl-[1,2,4]thiadiazol-5-yl)-3-aza-bicyclo[3.2.1]oct-8-yl]-[8-benzyloxy-[1,2,4]triazolo[1,5-a]pyridin-2-yl]-amine

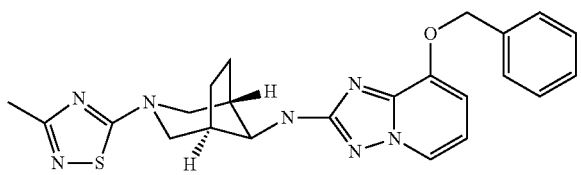 [SMILES: Cc1nsc(N2C[C@H]3CC[C@@H](C2)C3Nc2nc3c(OCc4ccccc4)cccn3n2)n1]

a) 8-Benzyloxy-2-bromo-[1,2,4]triazolo[1,5-a]pyridine

The title compound, a brown solid, (50 mg, crude), was prepared in analogy to example 7a from 8-benzyloxy-[1,2,4]triazolo[1,5-a]pyridine-2-yl-amine (CAS 1319067-83-8; WO 2011092272) (40 mg, 0.167 mmol).
MS ISP (m/e): 304.1/306.0 (98/100) [(M+H)+].

b) [(rac)-8-endo-3-(3-Methyl-[1,2,4]thiadiazol-5-yl)-3-aza-bicyclo[3.2.1]oct-8-yl]-[8-benzyloxy-[1,2,4]triazolo[1,5-a]pyridin-2-yl]-amine The title compound was prepared in analogy to example 6e from (rac)-8-endo-3-(3-methyl-[1,2,4]thiadiazol-5-yl)-3-aza-bicyclo[3.2.1]octan-8-amine (55.2 mg, 0.24 mmol) and 8-benzyloxy-2-bromo-[1,2,4]triazolo[1,5-a]pyridine (CAS 1319067-83-8; WO2011092272) (50 mg, 0.16 mmol) as a white solid (15.9 mg, 22%).
MS ISP (m/e): 448.0 (100) [(M+H)+].

EXAMPLE 15

[(rac)-8-endo-3-(3-Methyl-[1,2,4]thiadiazol-5-yl)-3-aza-bicyclo[3.2.1]oct-8-yl]-[5-propyl-[1,2,4]triazolo[1,5-a]pyridin-2-yl]-amine

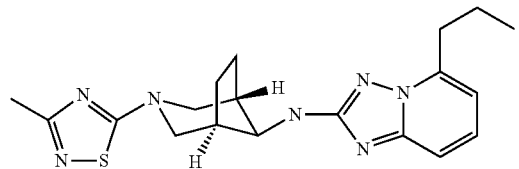 [SMILES: CCCc1cccc2nc(NC3[C@@H]4CC[C@H]3CN(c3nc(C)ns3)C4)nn12]

a) 2-Bromo-5-propyl-[1,2,4]triazolo-[1,5-a]pyridine

The title compound, a white solid, (53 mg, crude), was prepared in analogy to example 7a from 5-propyl-[1,2,4]triazolo[1,5-a]pyridine-2-yl-amine (CAS 1319067-63-4; WO 2011092272) (40 mg, 0.22 mmol).
MS ISP (m/e): 240.0/242.0 (96/100) [(M+H)+].

b) [(rac)-8-endo-3-(3-Methyl-[1,2,4]thiadiazol-5-yl)-3-aza-bicyclo[3.2.1]oct-8-yl]-[5-propyl-[1,2,4]triazolo[1,5-a]pyridin-2-yl]-amine The title compound was prepared in analogy to example 6e from (rac)-8-endo-3-(3-methyl-[1,2,4]thiadiazol-5-yl)-3-aza-bicyclo[3.2.1]octan-8-amine (70 mg, 0.31 mmol) and 2-bromo-5-propyl-[1,2,4]triazolo[1,5-a]pyridine (CAS 1319067-63-4; WO 2011092272) (50 mg, 0.20 mmol) as an off-white solid (11.2 mg, 14%).
MS ISP (m/e): 384.0 (100) [(M+H)+].
$^1$H NMR (DMSO-$d_6$, 400 MHz): δ (ppm)=7.40 (t, 1H), 7.29 (d, 1H), 6.76 (d, 1H), 6.67 (d, 1H), 3.85 (d, 1H), 3.57 (br m, 2H), 3.40 (d, 2H), 2.96 (t, 2H), 2.28 (s, 3H), 1.96 (m, 2H), 1.79 (q, 2H), 1.43 (br d, 2H), 0.95 (t, 3H).

EXAMPLE 16

[(rac)-8-endo-3-(3-Methyl-[1,2,4]thiadiazol-5-yl)-3-aza-bicyclo[3.2.1]oct-8-yl]-(5-phenyl-[1,2,4]triazolo[1,5-a]pyrazin-2-yl)-amine

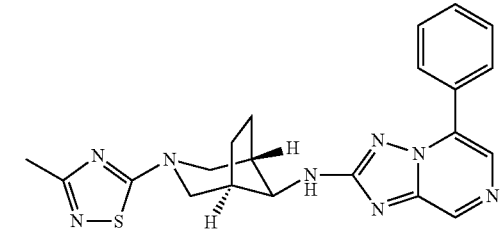 [SMILES: Cc1nsc(N2C[C@H]3CC[C@@H](C2)C3Nc2nc3cncc(-c4ccccc4)n3n2)n1]

a) 2-Amino-5-phenyl-[1,2,4]triazolo[1,5-a]pyrazine

To a solution of 6-(4-fluorophenyl)pyrazin-2-amine (1.484 g, 7.84 mmol) dissolved in dry dioxane (60 mL) was added ethoxycarbonyl isothiocyanate (1.02 mL, 8.63 mmol) to give a yellow suspension. The reaction mixture was stirred at room temperature for two days whereby the color turned from yellow to red and became a light brown suspension. The reaction mixture was evaporated to dryness under reduced pressure. The crude product was directly used for the next step (2.92 g, crude). MS ISP (m/e): 321.1 (100) [(M+H)$^+$].

The crude product was added to a suspension of hydroxylamine hydrochloride (2.72 g, 39.2 mmol) and N,N-diisopropylethyl amine (4.03 mL, 23.5 mmol) suspended in methanol (20 mL) and ethanol (20 mL). After stirring for 1 hour at room temperature, the reaction mixture was stirred at 60° C. for 3 hours. The reaction mixture was evaporated to dryness under reduced pressure and the residue was partitionated between saturated aqueous sodium hydrogen carbonate and methylene chloride. The organic layer was dried over sodium sulfate, filtered and the solvents evaporated under reduced pressure. The crude material was purified twice by flash chromatography (silica gel, 100 g, 0% to 15% MeOH/NH$_4$OH in dichloromethane) to yield the title compound as an off-white solid (985 mg, 55%).

MS ISP (m/e): 230.3 [(M+H)$^+$].

b) 2-Bromo-5-phenyl-(1,2,4)triazolo(1,5-a)pyrazine

The title compound was prepared in analogy to example 7a from 2-amino-5-phenyl-[1,2,4]triazolo[1,5-a]pyrazine (145.9 mg, 0.69 mmol)) as a light yellow crystalline solid (210 mg, quant.).

MS ISP (m/e): 277.1/275.1 (100/99) [(M+H)$^+$].

c) [(rac)-8-endo-3-(3-Methyl-[1,2,4]thiadiazol-5-yl)-3-aza-bicyclo[3.2.1]oct-8-yl]-(5-phenyl-[1,2,4]triazolo[1,5-a]pyrazin-2-yl)-amine The title compound was prepared in analogy to example 6e from (rac)-8-endo-3-(3-methyl-[1,2,4]thiadiazol-5-yl)-3-aza-bicyclo[3.2.1]octan-8-amine (42.6 mg, 0.19 mmol) and 2-bromo-5-phenyl-(1,2,4)triazolo(1,5-a)pyrazine (35 mg, 0.08 mmol) as a white solid (10.9 mg, 20%).

MS ISP (m/e): 419.4 (100) [(M+H)$^+$].

$^1$H NMR (DMSO-d$_6$, 400 MHz): δ (ppm)=8.92 (br s, 1H, NH), 8.24 (s, 1H), 8.09 (br d, 2H), 7.61-7.54 (m, 3H), 6.23 (d, 1H), 3.90 (d, 1H), 3.59 (br m, 2H), 3.39 (d, 2H), 2.95 (b s, 1H), 2.32 (s, 3H), 1.96 (m, 2H), 1.43 (br d, 2H).

EXAMPLE 17

[(rac)-8-endo-3-(3-Methyl-[1,2,4]thiadiazol-5-yl)-3-aza-bicyclo[3.2.1]oct-8-yl]-[5-trifluoromethyl-[1,2,4]triazolo[1,5-a]pyridin-2-yl]-amine

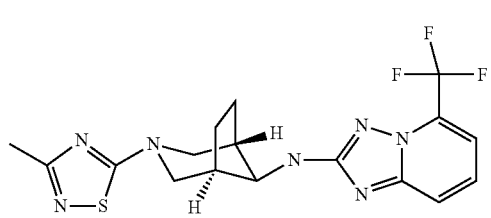 [SMILES: Cc1nsc(N2C[C@H]3CC[C@@H](C2)C3Nc2nc3cccc(C(F)(F)F)n3n2)n1]

a) 2-Bromo-5-trifluoromethyl[1,2,4]triazolo-[1,5-a]pyridine

The title compound, a brown solid, (60 mg, crude), was prepared in analogy to example 7a from 5-trifluoromethyl-[1,2,4]triazolo[1,5-a]pyridine-2-yl-amine (CAS 1319067-64-5; WO 2011092272) (50 mg, 0.248 mmol).

MS ISP (m/e): 266.0 [(M+H)$^+$].

b) [(rac)-8-endo-3-(3-Methyl-[1,2,4]thiadiazol-5-yl)-3-aza-bicyclo[3.2.1]oct-8-yl]-[5-trifluoromethyl-[1,2,4]triazolo[1,5-a]pyridin-2-yl]-amine The title compound was prepared in analogy to example 6e from (rac)-8-endo-3-(3-methyl-[1,2,4]thiadiazol-5-yl)-3-aza-bicyclo[3.2.1]octan-8-amine (63 mg, 0.28 mmol) and 2-bromo-(5-trifluoromethyl-[1,2,4]triazolo[1,5-a]pyridine-2-yl)amine (CAS 1319067-64-5; WO2011092272) (50 mg, 0.188 mmol) as an off-white solid (13.2 mg, 17%).

MS ISP (m/e): 410.2 (100) [(M+H)$^+$].

$^1$H NMR (DMSO-d$_6$, 400 MHz): δ (ppm)=7.80 (d, 1H), 7.61 (t, 1H), 7.48 (m, 1H), 7.13 (d, 1H), 3.88 (d, 1H), 3.57 (br m, 2H), 3.39 (d, 2H), 2.28 (s, 3H), 1.95 (m, 2H), 1.44 (br d, 2H).

EXAMPLE 18

[(rac)-8-endo-3-(3-Methyl-[1,2,4]thiadiazol-5-yl)-3-aza-bicyclo[3.2.1]oct-8-yl]-[6-chloro-8-(3,4-difluoro-phenyl)-[1,2,4]triazolo[1,5-a]pyridin-2-yl]-amine

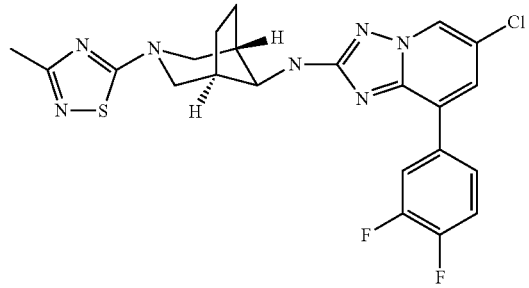 [SMILES: Cc1nsc(N2C[C@H]3CC[C@@H](C2)C3Nc2nc3c(-c4ccc(F)c(F)c4)cc(Cl)cn3n2)n1]

The title compound was prepared in analogy to example 6e from (rac)-8-endo-3-(3-methyl-[1,2,4]thiadiazol-5-yl)-3-aza-bicyclo[3.2.1]octan-8-amine (48.8 mg, 0.218 mmol) and 2-bromo-6-chloro-8-(3,4-difluoro-phenyl)-[1,2,4]triazolo[1,5-a]pyridine (CAS 1329673-51-9; US 20110201605) (50 mg, 0.145 mmol) as an off-white solid (10.2 mg, 14%). MS ISP (m/e): 488.2/490.2 (100/37) [(M+H)$^+$].

EXAMPLE 19

[(rac)-8-endo-3-(3-Methyl-[1,2,4]thiadiazol-5-yl)-3-aza-bicyclo[3.2.1]oct-8-yl]-[7-methyl-5-propyl-[1,2,4]triazolo[1,5-c]pyrimidin-2-yl]-amine

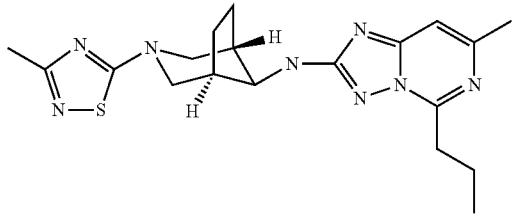

The title compound was prepared in analogy to example 6e from (rac)-8-endo-3-(3-methyl-[1,2,4]thiadiazol-5-yl)-3-aza-bicyclo[3.2.1]octan-8-amine (65.8 mg, 0.29 mmol) and 2-bromo-7-methyl-5-propyl-[1,2,4]triazolo[1,5-c]pyrimidine (CAS 1792-18-3; Miller, G. W.; Rose, F. L. *Journal of the Chemical Society* 1965, 3357-68) (50 mg, 0.196 mmol) as an off-white solid (8.8 mg, 11%). MS ISP (m/e): 399.2 (100) [(M+H)+].

EXAMPLE 20

[(rac)-8-endo-3-(3-Methyl-[1,2,4]thiadiazol-5-yl)-3-aza-bicyclo[3.2.1]oct-8-yl]-[8-(4,4-dimethyl-cyclohexyl)-[1,2,4]triazolo[1,5-a]pyridin-2-yl]-amine

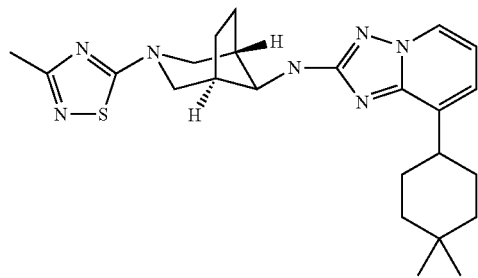 [SMILES: Cc1nsc(N2C[C@H]3CC[C@@H](C2)C3Nc2nc3c(C4CCC(C)(C)CC4)cccn3n2)n1]

a) N-(3-(1-Hydroxy-4,4-dimethylcyclohexyl)pyridin-2-yl)pivalamide

To a solution of N-(pyridin-2-yl)pivalamide (1.1 g, 6 mmol) in tetrahydrofurane (30 mL) was added at −78° C. under nitrogen and stirring a solution of 1.6M n-butyllithium in hexane (7.88 mL, 12.6 mmol). The reaction is exotherm and it turns light yellow. The reaction was stirred for 15 minutes at −78° C. and then for 2 hours at 0° C. The reaction was cooled to −78° C. and 4,4-dimethylcyclohexanone (937 mg, 7.2 mmol) dissolved in tetrahydrofurane (5 mL) was added dropwise. The reaction was warmed to room temperature over night. The reaction was quenched with saturated aqueous ammonium chloride solution and extracted twice with ethyl acetate. The combined organic layers were washed with saturated aqueous sodium chloride solution, dried over sodium sulfate, filtered and the solvent was evaporated under reduced pressure. The residue was purified by column chromatography on silica gel using ethyl acetate as the eluent to yield the title compound as a white powder (1.034 g, 57%).

MS ISP (m/e): 305.3 (15) [(M+H)+], 287.3 (93), 327.3 (100).

b) 3-(4,4-Dimethyl-cyclohex-1-enyl)-pyridin-2-ylamine

To a solution of N-(3-(1-hydroxy-4,4-dimethylcyclohexyl)pyridin-2-yl)pivalamide (1.034 g, 3.34 mmol) in ethanol (51 mL) was added 2M aqueous sodium hydroxide solution (16.98 mmol, 8.5 mL). The reaction was heated over night at 100° C. The solvent was evaporated under reduced pressure and the residue was partitionated between ethyl acetate and water. The aqueous layer was extracted twice with ethyl acetate and the organic layers were combined, dried over sodium sulfate, filtered and the solvent was removed under reduced pressure to yield the title compound as a white solid (706 mg, quant.). MS ISP (m/e): 203.3 (100) [(M+H)+].

c) N-[3-(4,4-Dimethyl-cyclohex-1-enyl)-pyridin-2-yl]-N''-carboethoxy-thiourea

To a solution of 3-(4,4-dimethyl-cyclohex-1-enyl)-pyridin-2-ylamine (704 mg, 3.48 mmol) in dioxane (21 mL) was added at room temperature ethoxycarbonylisothiocyanate (433 mL, 3.48 mmol). The reaction was stirred at room temperature over night and the solvent was removed to yield the crude product as a yellow oil (1.42 g, quant).

d) 8-(4,4-Dimethyl-cyclohex-1-enyl)-[1,2,4]triazolo[1,5-a]pyridin-2-ylamine

To a solution of N-[3-(4,4-dimethyl-cyclohex-1-enyl)-pyridin-2-yl]-N'-carboethoxy-thiourea (1.42 g, 3.48 mmol) in ethanol (4.3 mL) was added at room temperature hydroxylamine hydrochloride (1.50 g, 21.4 mmol) and methanol (4.3 mL). The yellow suspension was heated to 70° C. over night. The solvent was evaporated under reduced pressure and the residue was partitionated between ethyl acetate and water. The aqueous layer was extracted twice with ethyl acetate and the organic layers were combined, washed with saturated aqueous sodium chloride solution, dried over sodium sulfate, filtered and the solvent was removed under reduced pressure. The crude material was purified by column chromatography on silica gel first with ethyl acetate as the eluent and then once again with a mixture of heptane/ethyl acetate (1:1 v/v) as the eluent to yield the title compound as a yellow solid (526 mg, 51%).

MS ISP (m/e): 243.3 (100) [(M+H)+].

e) 8-(4,4-Dimethyl-cyclohexyl)-[1,2,4]triazolo[1,5-a]pyridine-2-ylamine

To a solution 8-(4,4-dimethyl-cyclohex-1-enyl)-[1,2,4]triazolo[1,5-a]pyridine-2-yl-amine (30 mg, 0.124 mmol) in methanol (4 mL) was added 10% Pd/C (30 mg), and the reaction mixture was allowed to stir under hydrogen balloon atmosphere at 25° C. for 2 hours. The reaction mixture was filtered through a bed of celite, and the filtrate was evaporated off in vacuo to get the title compound (30 mg, 99%) as a white solid which was used in next step without further purification. MS ISP (m/e): 245.0 (100) [(M+H)+].

f) 2-Bromo-8-(4,4-dimethyl-cyclohexyl)-[1,2,4]triazolo[1,5-c]pyridine

The title compound, a white solid, (43 mg, crude), was prepared in analogy to example 7a from 8-(4,4-dimethyl-cyclohexyl)-[1,2,4]triazolo[1,5-a]pyridine-2-ylamine (36 mg, 0.14 mmol). MS ISP (m/e): 308.2/310.2 (98/100) [(M+H)+].

g) [(rac)-8-endo-3-(3-Methyl-[1,2,4]thiadiazol-5-yl)-3-aza-bicyclo[3.2.1]oct-8-yl]-[8-(4,4-dimethyl-cyclohexyl)-[1,2,4]triazolo[1,5-a]pyridin-2-yl]-amine The title compound was prepared in analogy to example 6e from (r ac)-8-endo-3-(3-methyl-[1,2,4]thiadiazol-5-yl)-3-aza-bicyclo[3.2.1]octan-8-amine (46.9 mg, 0.209 mmol) and 2-bromo-8-(4,4-dimethyl-cyclohexyl)-(1,2,4)triazolo(1,5-a)

pyridine (43 mg, 0.14 mmol) as a white solid (12.3 mg, 19%). MS ISP (m/e): 452.2 (100) [(M+H)+].

EXAMPLE 21

[(rac)-8-endo-3-(3-Methyl-[1,2,4]thiadiazol-5-yl)-3-aza-bicyclo[3.2.1]oct-8-yl]-(7-furan-2-yl-[1,2,4]triazolo[1,5-a]pyrimidin-2-yl)-amine

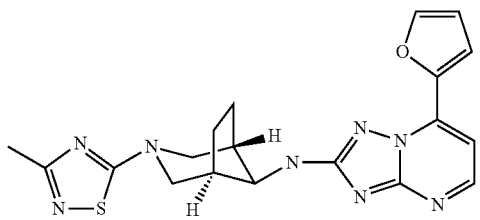 [SMILES: Cc1nsc(N2C[C@H]3CC[C@@H](C2)C3Nc2nc3nccc(-c4ccco4)n3n2)n1]

a) 2-Bromo-7-furan-2-yl-[1,2,4]triazolo[1,5-a]pyrimidine

The title compound, a brown solid, (50 mg, crude), was prepared in analogy to example 7a from 7-furan-2-yl-[1,2,4]triazolo[1,5-a]pyrimidine-2-yl-amine (CAS 338793-16-1; WO 2004005323) (30 mg, 0.14 mmol). MS ISP (m/e): 265.0 [(M+H)+].

b) [(rac)-8-endo-3-(3-Methyl-[1,2,4]thiadiazol-5-yl)-3-aza-bicyclo[3.2.1]oct-8-yl]-(7-furan-2-yl-[1,2,4]triazolo[1,5-a]pyrimidin-2-yl)-amine The title compound was prepared in analogy to example 6e from (rac)-8-endo-3-(3-methyl-[1,2,4]thiadiazol-5-yl)-3-aza-bicyclo[3.2.1]octan-8-amine (46.9 mg, 0.209 mmol) and 2-bromo-7-furan-2-yl-[1,2,4]triazolo[1,5-a]pyrimidine as a white solid (15.6 mg, 27%). MS ISP (m/e): 409.0 (100) [(M+H)+].

EXAMPLE 22

[(rac)-8-endo-3-(3-Methyl-[1,2,4]thiadiazol-5-yl)-3-aza-bicyclo[3.2.1]oct-8-yl]-[7-trifluoromethyl-[1,2,4]triazolo[1,5-a]pyridin-2-yl]-amine

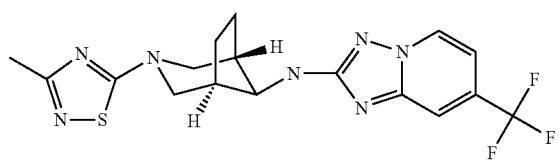 [SMILES: Cc1nsc(N2C[C@H]3CC[C@@H](C2)C3Nc2nc3cc(C(F)(F)F)ccn3n2)n1]

a) 2-Bromo-7-trifluoromethyl[1,2,4]triazolo[1,5-a]pyridine

The title compound, a brown solid, (39 mg, crude), was prepared in analogy to example 7a from 7-trifluoromethyl-[1,2,4]triazolo[1,5-a]pyridine-2-yl-amine (CAS 1260811-97-9; WO 2011092272) (30 mg, 0.14 mmol).
MS ISP (m/e): 266.0/268.0 (85/100) [(M+H)+].

b) [(rac)-8-endo-3-(3-Methyl-[1,2,4]thiadiazol-5-yl)-3-aza-bicyclo[3.2.1]oct-8-yl]-[7-trifluoromethyl-[1,2,4]triazolo[1,5-a]pyridin-2-yl]-amine The title compound was prepared in analogy to example 6e from (rac)-8-endo-3-(3-methyl-[1,2,4]thiadiazol-5-yl)-3-aza-bicyclo[3.2.1]octan-8-amine (49.2 mg, 0.22 mmol) and 2-bromo-7-trifluoromethyl-[1,2,4]triazolo[1,5-a]pyridine (educt amine CAS 1260811-97-9; WO 2011092272) (39 mg, 0.147 mmol) as an off-white solid (25.1 mg, 42%). MS ISP (m/e): 410.2 (100) [(M+H)+].

EXAMPLE 23

[(rac)-8-endo-3-(3-Methyl-[1,2,4]thiadiazol-5-yl)-3-aza-bicyclo[3.2.1]oct-8-yl]-[8-(4-trifluoromethyl-cyclohexyl)-[1,2,4]triazolo[1,5-a]pyridin-2-yl]-amine

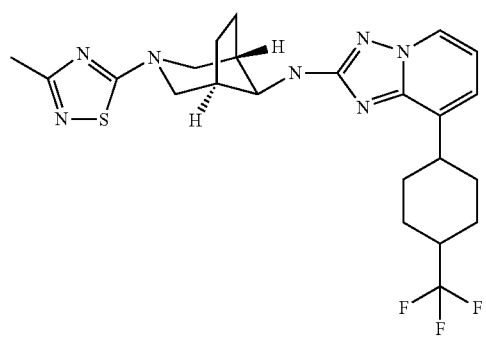 [SMILES: Cc1nsc(N2C[C@H]3CC[C@@H](C2)C3Nc2nc3c(C4CCC(C(F)(F)F)CC4)cccn3n2)n1]

a) 8-(4-Trifluoromethyl-cyclohexyl)-[1,2,4]triazolo[1,5-a]pyridine-2-yl-amine

To a solution 8-(4-trifluoromethyl-cyclohexenyl)-[1,2,4]triazolo[1,5-a]pyridine-2-ylamine (CAS 1329673-42-8, US 20110201605) (30 mg, 0.106 mmol) in methanol (5 mL) was added 10% Pd/C (30 mg), and the reaction mixture was allowed to stir at 25° C. for 2 hours under hydrogen balloon atmosphere. The reaction mixture was filtered through a bed of celite and the filtrate was evaporated off in vacuo yield the title compound as a white solid (30 mg, 99%) which was used in the next step without further purification. MS ISP (m/e): 285.2 (100) [(M+H)+].

b) 2-Bromo-8-(4-trifluoromethyl-cyclohexyl)-[1,2,4]triazolo[1,5-a]pyridine

The title compound, a white solid, (37 mg, crude), was prepared in analogy to example 7a from 8-(4-trifluoromethyl-cyclohexyl)-[1,2,4]triazolo[1,5-a]pyridine-2-yl-amine (30 mg, 0.10 mmol). MS ISP (m/e): 348.0/350.0 (100/85) [(M+H)+].

c) [(rac)-8-endo-3-(3-Methyl-[1,2,4]thiadiazol-5-yl)-3-aza-bicyclo[3.2.1]oct-8-yl]-[8-(4-trifluoromethyl-cyclohexyl)-[1,2,4]triazolo[1,5-a]pyridin-2-yl]-amine The title compound was prepared in analogy to example 6e from (rac)-8-endo-3-(3-methyl-[1,2,4]thiadiazol-5-yl)-3-aza-bicyclo[3.2.1]octan-8-amine (34.2 mg, 0.15 mmol) and 2-bromo-8-(4-trifluoromethyl-cyclohexyl)-[1,2,4]triazolo
(1,5-a)pyridine (37 mg, 0.10 mmol) as a light brown solid (4
mg, 8%).

MS ISP (m/e): 499.2 (100) [(M+H)+].

EXAMPLE 24

[(rac)-8-endo-3-(6-Methyl-pyrimidin-4-yl)-6-oxa-3-aza-bicyclo[3.2.1]oct-8-yl]-[8-(2,3,4-trifluoro-phenyl)-[1,2,4]triazolo[1,5-a]pyridin-2-yl]-amine

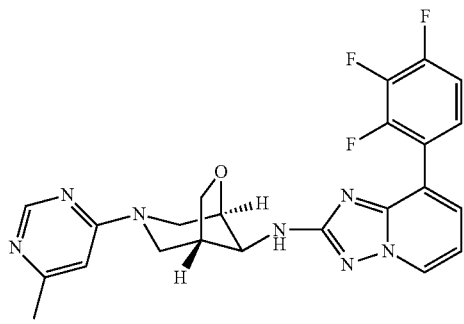 [SMILES: Cc1cc(N2C[C@@H]3CO[C@H](C2)C3Nc2nc3c(-c4ccc(F)c(F)c4F)cccn3n2)ncn1]

a) (rac)-3-Benzyl-6-oxa-3-aza-bicyclo[3.2.1]octan-8-one

A solution of benzylamine (1.26 mL, 11.6 mmol) in methanol (2 mL) was added drop wise to a refluxing solution of dihydro-furan-3-one (1 g, 11.6 mmol), paraformaldehyde (1.04 g, 34.84 mmol), and glacial acetic acid (0.67 mL, 11.61 mmol) in methanol (8 mL) over a period of 3 hours under nitrogen. Reflux was continued for 1 hour after which, the brown reaction mixture was stirred at 23° C. for 16 hours. The reaction mixture was concentrated in vacuo. The resulting oil was diluted with water and basified with 6 N aqueous NaOH solution. The aqueous solution was extracted with ethyl acetate, washed with water, brine, dried over sodium sulfate, filtered and concentrated under reduced pressure. The crude product was purified by flash column chromatography on silica gel with 25-30% ethyl acetate in hexane as eluent. The title compound was obtained as a colorless sticky liquid (500 mg, 20%).

b) (rac)-3-Benzyl-6-oxa-3-aza-bicyclo[3.2.1]octan-8-one oxime

A mixture of (rac)-3-benzyl-6-oxa-3-aza-bicyclo[3.2.1]octan-8-one (500 mg, 2.30 mmol), hydroxylamine hydrochloride (224 mg, 3.22 mmol) and pyridine (0.32 mL) in ethanol (5 mL) was heated to 100° C. for 2 hours. The reaction mixture was concentrated under reduced pressure. 2.5 N Aqueous sodium hydroxide solution (10 mL) was added to the residue. The resulting solution was extracted with ethyl acetate (50 mL), washed with water and brine, dried over anhydrous sodium sulfate, filtered and concentrated under reduced pressure. The crude product was purified by column chromatography on silica gel with 5-10% ethyl acetate/hexane mixture as eluent to afford the title compound as a brown sticky liquid (220 mg, 43%).

c) (rac)-8-endo-3-Benzyl-6-oxa-3-aza-bicyclo[3.2.1]oct-8-ylamine

To a de-oxygentated solution of (rac)-3-benzyl-6-oxa-3-aza-bicyclo[3.2.1]octan-8-one oxime (6.6 g, 28.4 mmol) in methanol (140 mL) was added Raney nickel (1.36 g) under an argon atmosphere. It was hydrogenated using a hydrogen balloon at 23° C. for 1 hour. The reaction was filtered through a bed of celite and the filtrate was concentrated to dryness. The crude residue was purified by flash column chromatography on silica gel (0.5 to 1.5% methanol in dichloromethane as eluent). A mixture of exo- and endo-isomers was obtained. The column chromatography was repeated twice to afford the endo-isomer as a colorless oil (260 mg, 42%).

d) ((rac)-8-endo-3-Benzyl-6-oxa-3-aza-bicyclo[3.2.1]oct-8-yl)-[8-(2,3,4-trifluoro-phenyl)-[1,2,4]triazolo[1,5-a]pyridin-2-yl]-amine A solution of 2-bromo-8-(2,3,4-trifluoro-phenyl)-[1,2,4]triazolo[1,5-a]pyridine (100 mg, 0.30 mmol), (rac)-8-endo-3-benzyl-6-oxa-3-aza-bicyclo[3.2.1]oct-8-ylamine (66 mg, 0.305 mmol) and sodium phenoxide (45 mg, 0.39 mmol) in dry 1,4-dioxane (4 mL) in a microwave vial was purged with argon for 10 minutes. Pd$_2$(dba)$_3$.CHCl$_3$ (11 mg, 0.011 mmol) and xanthphos (13 mg, 0.022 mmol) were added to the solution and degassing continued for another 5 minutes before the reaction mixture was heated at 130° C. for 30 minutes in a microwave. The reaction was diluted with dichloromethane (20 mL), washed with 1M aqueous sodium carbonate solution (1×30 mL). The organic phase was dried over sodium sulfate, filtered and the solvent was evaporated under reduced pressure. The residue was purified by flash column chromatography on silica gel using MeOH/dichloromethane (3%) as eluent to afford the title compound as a light brown solid (85 mg, 59%).

e) (rac)-8-endo-6-Oxa-3-aza-bicyclo[3.2.1]oct-8-yl-[8-(2,3,4-trifluoro-phenyl)-[1,2,4]triazolo[1,5-a]pyridin-2-yl]-amine To a de-oxygentated solution of ((rac)-8-endo-3-benzyl-6-oxa-3-aza-bicyclo[3.2.1]oct-8-yl)-[8-(2,3,4-trifluoro-phenyl)-[1,2,4]triazolo[1,5-a]pyridin-2-yl]-amine (85 mg, 0.18 mmol) in methanol (15 mL) was added 10% palladium on charcoal (19 mg) and few drops of 25% aqueous hydrochloric acid solution. The reaction mass was stirred under a hydrogen balloon at atmospheric pressure and at 23° C. for 2 days. The reaction mass was filtered through a bed of celite and the filtrate was evaporated to dryness under reduced pressure to afford the title compound as a brown sticky solid (68 mg, 99%).

f) [(rac-8-endo-3-(6-Methyl-pyrimidin-4-yl)-6-oxa-3-aza-bicyclo[3.2.1]oct-8-yl]-[8-(2,3,4-trifluoro-phenyl)-[1,2,4]triazolo[1,5-a]pyridin-2-yl]-amine To a solution of (rac)-8-endo-6-oxa-3-aza-bicyclo[3.2.1]oct-8-yl-[8-(2,3,4-trifluoro-phenyl)-[1,2,4]triazolo[1,5-a]pyridin-2-yl]-amine (68 mg, 0.181 mmol) in NMP (1 mL) was added triethylamine until the pH of the resulting solution was basic. To this reaction was added 4-chloro-6-methyl-pyrimidine (70 mg, 0.544 mmol) and the mixture was heated to 135° C. for 2 hours. The reaction mass was cooled and partitioned between ethyl acetate (50 mL) and water (10 mL). The organic phase was dried over anhydrous sodium sulfate and concentrated to dryness under reduced pressure. The resulting crude residue was purified by preparative HPLC using acetonitrile and aqueous ammonium acetate buffer as solvent and Xbridge column to afford the title compound as a light brown solid (24.0 mg, 28%).

MS ISP (m/e): 468.4 [(M+H)+].

EXAMPLE 25

[(rac)-9-exo-7-(6-Methyl-pyrimidin-4-yl)-3-thia-7-aza-bicyclo[3.3.1]non-9-yl]-[8-(2,3,4-trifluoro-phenyl)-[1,2,4]triazolo[1,5-a]pyridin-2-yl]-amine

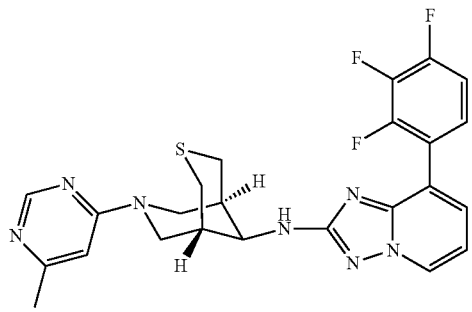 [SMILES: Cc1cc(N2C[C@H]3CSC[C@@H](C2)C3Nc2nc3c(-c4ccc(F)c(F)c4F)cccn3n2)ncn1]

a) (rac)-7-Benzyl-3-thia-7-aza-bicyclo[3.3.1]nonan-9-one

The title compound was prepared in analogy to example 24a from tetrahydro-thiopyran-4-one (10 g, 86.0 mmol) as a light yellow solid (4 g, 17%).

b) (rac)-7-Benzyl-3-thia-7-aza-bicyclo[3.3.1]nonan-9-one oxime

The title compound was prepared in analogy to example 24b from (rac)-7-benzyl-3-thia-7-aza-bicyclo[3.3.1]nonan-9-one as a solid (2.4 g, 90%).

c) (rac)-9-exo-7-Benzyl-3-thia-7-aza-bicyclo[3.3.1]non-9-ylamine

The title compound was prepared in analogy to example 24c from (rac)-7-benzyl-3-oxa-7-aza-bicyclo[3.3.1]nonan-9-one oxime (1.5 g, 5.7 mmol) as a solid (150 mg, 10%).

d) ((rac)-9-exo-7-Benzyl-3-thia-7-aza-bicyclo[3.3.1]non-9-yl)-[842,3,4-trifluoro-phenyl)-[1,2,4]triazolo[1,5-a]pyridin-2-yl]-amine The title compound was prepared in analogy to example 24d from 2-bromo-8-(2,3,4-trifluoro-phenyl)-[1,2,4]triazolo[1,5-a]pyridine (150 mg, 0.457 mmol) and (rac)-9-exo-7-benzyl-3-thia-7-aza-bicyclo[3.3.1]non-9-ylamine (124.7 mg, 0.503 mmol) as a light brown solid (90.0 mg, 39%).

e) ((rac)-9-exo-3-Thia-7-aza-bicyclo[3.3.1]non-9-yl)-[8-(2,3,4-trifluoro-phenyl)-[1,2,4]triazolo[1,5-a]pyridin-2-yl]-amine The title compound was prepared in analogy to example 24e from ((rac)-9-exo-7-benzyl-3-thia-7-aza-bicyclo[3.3.1]non-9-yl)-[8-(2,3,4-trifluoro-phenyl)-[1,2,4]triazolo[1,5-a]pyridin-2-yl]-amine (90 mg, 0.182 mmol) as a light yellow solid (70.0 mg, 95%).

f) [(rac)-9-exo-7-(6-Methyl-pyrimidin-4-yl)-3-thia-7-aza-bicyclo[3.3.1]non-9-yl]-[8-(2,3,4-trifluoro-phenyl)-[1,2,4]triazolo[1,5-a]pyridin-2-yl]-amine The title compound was prepared in analogy to example 24f from ((rac)-9-exo-3-thia-7-aza-bicyclo[3.3.1]non-9-yl)-[8-(2,3,4-trifluoro-phenyl)-[1,2,4]triazolo[1,5-a]pyridin-2-yl]-amine (70 mg, 0.173 mmol) as a light brown solid (8.7 mg, 10%).

MS ISP (m/e): 498.4 [(M+H)$^+$].

EXAMPLE 26

[(rac)-9-endo-3-(6-Methyl-pyrimidin-4-yl)-3-aza-bicyclo[3.3.1]non-9-yl]-[8-(2,3,4-trifluoro-phenyl)-[1,2,4]triazolo[1,5-a]pyridin-2-yl]-amine

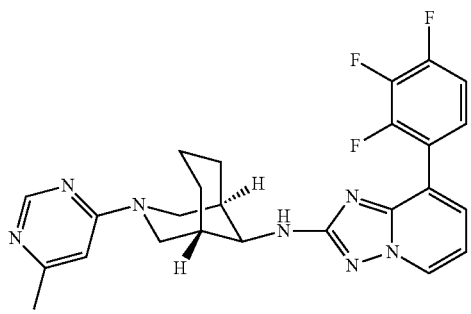 [SMILES: Cc1cc(N2C[C@H]3CCC[C@@H](C2)C3Nc2nc3c(-c4ccc(F)c(F)c4F)cccn3n2)ncn1]

a) (rac)-3-Benzyl-3-aza-bicyclo[3.3.1]nonan-9-one oxime

The title compound was prepared in analogy to example 24b from 3-benzyl-3-aza-bicyclo[3.3.1]nonan-9-one (commercial available) (1.5 g, 6.54 mmol) as an oily liquid (1.4 g, 87%).

b) (rac)-9-endo/exo-3-Benzyl-3-aza-bicyclo[3.3.1]non-9-ylamine

The title compound was prepared in analogy to example 24c from (rac)-3-benzyl-3-aza-bicyclo[3.3.1]nonan-9-one oxime (1.4 g, 5.72 mmol) as a light yellow solid (1.2 g, 91%).

c) ((rac)-9-endo/exo-3-Benzyl-3-aza-bicyclo[3.3.1]non-9-yl)-[8-(2,3,4-trifluoro-phenyl)-[1,2,4]triazolo[1,5-a]pyridin-2-yl]-amine The title compound was prepared in analogy to example 24d from 2-bromo-8-(2,3,4-trifluoro-phenyl)-[1,2,4]triazolo[1,5-a]pyridine (200 mg, 0.61 mmol) and (rac)-9-endo/exo-3-benzyl-3-aza-bicyclo[3.3.1]non-9-ylamine (140 mg, 0.457 mmol) as a light brown sticky solid (80 mg, 27%).

d) arac)-9-endo/exo-3-Aza-bicyclo[3.3.1]non-9-yl)-[8-(2,3,4-trifluoro-phenyl)-[1,2,4]triazolo[1,5-a]pyridin-2-yl]-amine The title compound was prepared in analogy to example 24e from ((rac)-9-endo/exo-3-benzyl-3-aza-bicyclo[3.3.1]non-9-yl)-[8-(2,3,4-trifluoro-phenyl)-[1,2,4]triazolo[1,5-a]pyridin-2-yl]-amine (65 mg, 0.165 mmol) as a brown sticky solid (64 mg, 99%).

e) [(rac-9-endo-3-(6-Methyl-pyrimidin-4-yl)-3-aza-bicyclo[3.3.1]non-9-yl]-[8-(2,3,4-trifluoro-phenyl)-[1,2,4]triazolo[1,5-a]pyridin-2-yl]-amine The title compound was prepared in analogy to example 24f from ((rac)-9-endo/exo-3-aza-bicyclo[3.3.1]non-9-yl)-

[8-(2,3,4-trifluoro-phenyl)-[1,2,4]triazolo[1,5-a]pyridin-2-yl]-amine (80 mg, 0.166 mmol) as a light brown solid (6.0 mg, 7.6%).

MS ISP (m/e): 480.4 [(M+H)$^+$].

EXAMPLE 27

[(rac)-9-exo-7-(6-Methyl-pyrimidin-4-yl)-3-oxa-7-aza-bicyclo[3.3.1]non-9-yl]-[8-(2,3,4-trifluoro-phenyl)-[1,2,4]triazolo[1,5-a]pyridin-2-yl]-amine

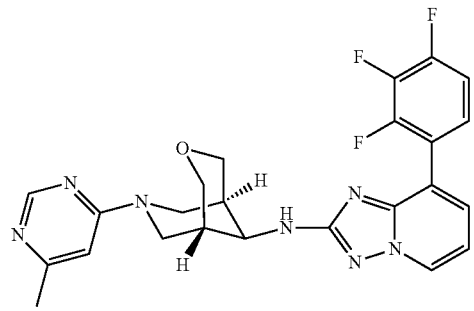 [SMILES: Cc1cc(N2C[C@H]3COC[C@@H](C2)C3Nc2nc3c(-c4ccc(F)c(F)c4F)cccn3n2)ncn1]

a) (rac)-3-Benzyl-3-aza-bicyclo[3.3.1]nonan-9-one

The title compound was prepared in analogy to example 24a from tetrahydro-pyran-4-one (10 g, 99 mmol) as a light yellow oil (4 g, 17%).

b) (rac)-7-Benzyl-3-oxa-7-aza-bicyclo[3.3.1]nonan-9-one oxime

The title compound was prepared in analogy to example 24b from (rac)-3-benzyl-3-aza-bicyclo[3.3.1]nonan-9-one (4 g, 17.3 mmol) as an oily liquid (4 g, 94%).

c) (rac)-9-endo/exo-7-Benzyl-3-oxa-7-aza-bicyclo[3.3.1]non-9-ylamine

The title compound was prepared in analogy to example 24c from (rac)-7-benzyl-3-oxa-7-aza-bicyclo[3.3.1]nonan-9-one oxime (5 g, 20.3 mmol) as a solid (4 g, 85%).

d) (rac)-9-endo/exo-7-Benzyl-3-oxa-7-aza-bicyclo[3.3.1]non-9-yl)-[8-(2,3,4-trifluoro-phenyl)-[1,2,4]triazolo[1,5-a]pyridin-2-yl]-amine The title compound was prepared in analogy to example 24d from 2-bromo-8-(2,3,4-trifluoro-phenyl)-[1,2,4]triazolo[1,5-a]pyridine (150 mg, 0.45 mmol) and (rac)-9-endo/exo-7-benzyl-3-oxa-7-aza-bicyclo[3.3.1]non-9-ylamine (116.7 mg, 0.50 mmol) as a light brown solid (150 mg, 68%).

e) (rac)-9-endo/exo-3-Oxa-7-aza-bicyclo[3.3.1]non-9-yl)-[8-(2,3,4-trifluoro-phenyl)-[1,2,4]triazolo[1,5-a]pyridin-2-yl]-amine The title compound was prepared in analogy to example 24e from (rac)-9-endo/exo-7-benzyl-3-oxa-7-aza-bicyclo[3.3.1]non-9-yl)-[8-(2,3,4-trifluoro-phenyl)-[1,2,4]triazolo[1,5-a]pyridin-2-yl]-amine (150 mg, 0.313 mmol) as a light yellow solid (120 mg, 98%).

f) [(rac)-9-exo-7-(6-Methyl-pyrimidin-4-yl)-3-oxa-7-aza-bicyclo[3.3.1]non-9-yl]-[8-(2,3,4-trifluoro-phenyl)-[1,2,4]triazolo[1,5-a]pyridin-2-yl]-amine The title compound was prepared in analogy to example 24f from (rac)-9-endo/exo-3-oxa-7-aza-bicyclo[3.3.1]non-9-yl)-[8-(2,3,4-trifluoro-phenyl)-[1,2,4]triazolo[1,5-a]pyridin-2-yl]-amine (121 mg, 0.311 mmol) as a light brown solid (20.9 mg, 14%).

MS ISP (m/e): 482.4 [(M+H)$^+$].

EXAMPLE 28

[(rac)-8-exo-Methyl-3-(6-methyl-pyrimidin-4-yl)-3-aza-bicyclo[3.2.1]oct-8-endo-yl]-[8-(2,3,4-trifluoro-phenyl)-[1,2,4]triazolo[1,5-a]pyridin-2-yl]-amine

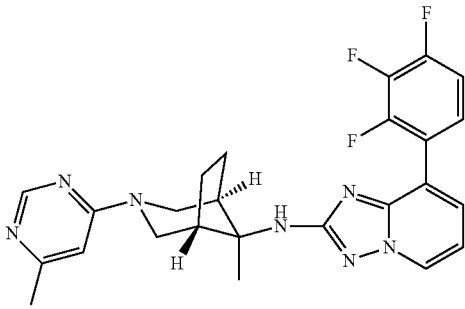 [SMILES: Cc1cc(N2C[C@H]3CC[C@@H](C2)C3(C)Nc2nc3c(-c4ccc(F)c(F)c4F)cccn3n2)ncn1]

a) (Rac)-8-endo/exo-3-Benzyl-8-endo/exo-methyl-3-aza-bicyclo[3.2.1]octan-8-ol

To the solution of (rac)-3-benzyl-3-aza-bicyclo[3.2.1]octan-8-one (7 g, 32.5 mmol) in dry tetrahydrofurane (100 mL) was added a solution of methyl magnesium bromide in THF (1.4 M, 104 mL, 146.5 mmol) at −20° C. with a syringe under an atmosphere of nitrogen. The reaction mixture was stirred at −20° C. for 30 minutes, and then at 23° C. for 16 hours. The reaction mixture was quenched with saturated aqueous ammonium chloride solution and extracted with ethyl acetate (3×75 mL), washed with water and brine, dried over anhydrous sodium sulfate and concentrated to dryness under reduced pressured. The crude residue was purified by flash column chromatography on silica gel (15-20% ethyl acetate in hexane as eluent) to afford the title compound (5 g, 66%) as pale yellow oil.

b) N-((rac)-3-Benzyl-8-exo-methyl-3-aza-bicyclo[3.2.1]oct-8-endo-yl)-acetamide

To a solution of (rac)-8-endo/exo-3-benzyl-8-endo I exo-methyl-3-aza-bicyclo[3.2.1]octan-8-ol (5.4 g, 23.3 mmol) in acetonitrile (27 mL) was added concentrated sulfuric acid (22 mL) at 23° C. over a period of 10 minutes. The reaction mixture was stirred at 23° C. for 16 hours. The reaction mixture was poured into ice and the resulting solution was adjusted to pH 10 with aqueous potassium hydroxide solution. It was extracted with ethyl acetate (3×50 mL) and washed with water and brine, dried over anhydrous sodium sulfate, filtered and concentrated under reduced pressure. The crude residue was purified by flash column chromatography on silica gel (25-30% ethyl acetate in hexane as eluent) to afford the title compound as a light yellow solid (1 g, 16%).

c) (rac)-3-Benzyl-8-exo-methyl-3-aza-bicyclo[3.2.1]oct-8-endo-ylamine

To a solution of 3-N-((rac)-3-benzyl-8-exo-methyl-3-aza-bicyclo[3.2.1]oct-8-endo-yl)-acetamide (1 g, 3.67 mmol) in 6N aqueous HCl solution (40 mL) was refluxed for 36 hours. The reaction mixture was made alkaline (pH=11) with 20% aqueous NaOH solution and extracted with ethyl acetate (3×50 mL), washed with water and brine, dried over anhydrous sodium sulfate, filtered and concentrated to dryness under reduced pressure. The crude residue was purified by flash column chromatography on silica gel (2 to 3.5% methanol in dichloromethane as eluent) to afford the title compound as a light brown semi solid (225 mg, 27%).

d) (rac)-3-Benzyl-8-exo-methyl-3-aza-bicyclo[3.2.1]oct-8-endo-yl)-[8-(2,3,4-trifluoro-phenyl)-[1,2,4]triazolo[1,5-a]pyridin-2-yl]-amine The title compound was prepared in analogy to example 24d from 2-bromo-8-(2,3,4-trifluoro-phenyl)-[1,2,4]triazolo[1,5-a]pyridine (100 mg, 0.305 mmol) and (rac)-3-benzyl-8-exo-methyl-3-aza-bicyclo[3.2.1]oct-8-endo-ylamine (77.1 mg, 0.335 mmol) as a light brown solid (60 mg, 41%).

e) (rac)-8-exo-Methyl-3-aza-bicyclo[3.2.1]oct-8-endo-yl)-[8-(2,3,4-trifluoro-phenyl)-[1,2,4]triazolo[1,5-a]pyridin-2-yl]-amine The title compound was prepared in analogy to example 24e from (rac)-3-benzyl-8-exo-methyl-3-aza-bicyclo[3.2.1]oct-8-endo-yl)-[8-(2,3,4-trifluoro-phenyl)-[1,2,4]triazolo[1,5-a]pyridin-2-yl]-amine (44 mg, 0.092 mmol) as a light yellow solid (35 mg, 98%).

f) [(rac)-8-exo-Methyl-3-(6-methyl-pyrimidin-4-yl)-3-aza-bicyclo[3.2.1]oct-8-endo-yl]-[8-(2,3,4-trifluoro-phenyl)-[1,2,4]triazolo[1,5-a]pyridin-2-yl]-amine The title compound was prepared in analogy to example 24f from (rac)-3-benzyl-8-exo-methyl-3-aza-bicyclo[3.2.1]oct-8-endo-yl)-[8-(2,3,4-trifluoro-phenyl)-[1,2,4]triazolo[1,5-a]pyridin-2-yl]-amine (35 mg, 0.09 mmol) as a light brown solid (1.8 mg, 4.2%). MS ISP (m/e): 480.4 [(M+H)$^+$].

EXAMPLE 29

[(rac)-8-(4-Fluoro-phenyl)-5,6,7,8-tetrahydro-[1,2,4]triazolo[1,5-a]pyridin-2-yl]-[(rac)-8-exo-3-(3-methyl-[1,2,4]thiadiazol-5-yl)-3-aza-bicyclo[3.2.1]oct-8-yl]-amine

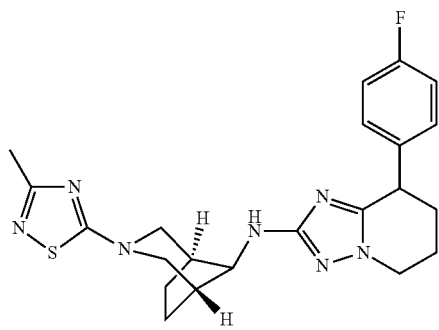 [SMILES: Cc1nsc(N2C[C@H]3CC[C@@H](C2)C3Nc2nc3n(n2)CCCC3c2ccc(F)cc2)n1]

a) N-((rac)-8-exo-3-benzyl-3-azabicyclo[3.2.1]octan-8-yl)-(rac)-8-(4-fluorophenyl)-5,6,7,8-tetrahydro-[1,2,4]triazolo[1,5-a]pyridin-2-amine To a solution of (rac)-8-(4-fluorophenyl)-5,6,7,8-tetrahydro-[1,2,4]triazolo[1,5-a]pyridin-2-amine (CAS 1262197-53-4; US 20110201605) (128 mg, 551 µmol) and (rac)-3-benzyl-3-azabicyclo[3.2.1]octan-8-one (178 mg, 827 µmol) in 1,2-dichloroethane (5 mL) was added under stirring and under an atmosphere of nitrogen titanium isopropoxide (470 mg, 489 µL, 1.65 mmol) and stirred at 85° C. overnight. After cooling to room temperature, ethanol (5 mL) was added and then carefully sodium borohydride (83.4 mg, 2.2 mmol). The reaction was stirred overnight at 85° C. After cooling, water was added and the reaction was stirred for 30 minutes. The precipitation was filtered off and washed with ethanol. The filtrate was concentrated under reduced pressure and water was added. The reaction was extracted twice with ethyl acetate. The combined organic layers were washed with brine, dried over sodium sulfate, filtered and the solvent was evaporated under reduced pressure. The residue was purified by column chromatography on silica gel using methylene chloride to methylene chloride/methanol (v/v 19:1) as eluent. The title compound was obtained crude (84 mg) as a yellow viscous oil and was used in the next step without further purification. MS ISP (m/e): 432.4 (100) [(M+H)$^+$], 218.3 (87), 275.2 (24).

b) N-arac)-8-exo-3-azabicyclo[3.2.1]octan-8-yl)-(rac)-8-(4-fluorophenyl)-5,6,7,8-tetrahydro-[1,2,4]triazolo[1,5-a]pyridin-2-amine hydro chloride To a solution of N-((rac)-8-exo-3-benzyl-3-azabicyclo[3.2.1]octan-8-yl)-8-(rac)-8-(4-fluorophenyl)-5,6,7,8-tetrahydro-[1,2,4]triazolo[1,5-a]pyridin-2-amine (84 mg, 195 mmol) in methanol (1.95 mL) was added one drop of 25% aqueous hydrogen chloride solution and Pd/C 10% (20.7 mg, 195 µmol). The reaction was hydrogenated under an atmosphere of hydrogen overnight. The catalyst was filtered off and washed with methanol. The filtrate was evaporated under reduced pressure to yield the title compound as light brown solid (80 mg). The crude material was used without further purification directly in the next step.

c) [(rac)-8-(4-Fluoro-phenyl)-5,6,7,8-tetrahydro-[1,2,4]triazolo[1,5-a]pyridin-2-yl]-[(rac)-8-exo-3-(3-methyl-[1,2,4]thiadiazol-5-yl)-3-aza-bicyclo[3.2.1]oct-8-yl]-amine To a solution of N-((rac)-8-exo-3-azabicyclo[3.2.1]octan-8-yl)-(rac)-8-(4-fluorophenyl)-5,6,7,8-tetrahydro-[1,2,4]triazolo[1,5-a]pyridin-2-amine hydrochloride (79 mg, 209 µmol) in ethanol (1 mL) was added triethylamine (63.5 mg, 87.4 µL, 627 µmol) and 5-chloro-3-methyl-1,2,4-thiadiazole (38.5 mg, 272 µmol) dissolved in ethanol (0.5 mL). The reaction was stirred over night at 100° C. The solvent was evaporated under reduced pressure and the residue was purified by column chromatography using a gradient from methylenechloride to a mixture of methylenechloride/methanol (v/v 19:1) as eluent. The compound was purified a second time on silica gel using a gradient from ethyl acetate to a mixture of ethyl acetate/methanol (v/v 9:1) as eluent to yield the title compound as a light yellow solid (33 mg, 36%). MS ISP (m/e): 440.5 (100) [(M+H)$^+$].

EXAMPLE 30

[8-(3,4-Difluoro-phenyl)-[1,2,4]triazolo[1,5-a]pyridin-2-yl]-[(rac)-8-endo-3-(2-methyl-pyrimidin-4-yl)-3-aza-bicyclo[3.2.1]oct-8-yl]-amine

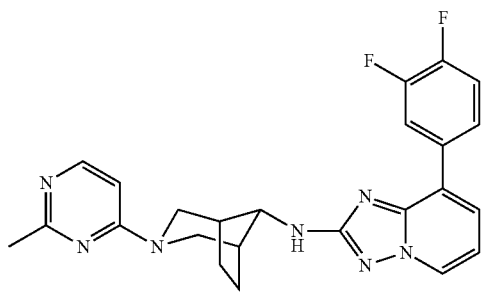 [SMILES: Cc1nccc(N2CC3CCC(C2)C3Nc2nc3c(-c4ccc(F)c(F)c4)cccn3n2)n1]

a) N-((rac)-8-endo-3-benzyl-3-azabicyclo[3.2.1]octan-8-yl)-8-(3,4-difluorophenyl)-[1,2,4]triazolo[1,5-a]pyridin-2-amine To a solution of 2-bromo-8-(3,4-difluorophenyl)-[1,2,4]triazolo[1,5-a]pyridine (CAS 1329672-92-5; US 20110201605) (372 mg, 1.2 mmol) and (rac)-8-endo-3-benzyl-3-azabicyclo[3.2.1]octan-8-amine (216 mg, 1 mmol) in dioxane (7 mL) was added under an atmosphere of nitrogen and under stirring sodium phenoxide (183 mg, 1.5 mmol), 4,5-bis(diphenylphosphin)-9,9-dimethylxanthene (94.5 mg, 160 µmol) and tris(dibenzylideneacetone)dipalladium (0) chloroform adduct (85.4 mg, 80.0 µmol). The reaction was degassed three times and heated to 130° C. for 30 minutes in a microwave oven. It was diluted with methylenchloride, washed with 1M aqueous sodium carbonate solution and with saturated aqueous sodium chloride solution, dried over sodium sulfate, filtered and the solvent was removed under reduced pressure. The residue was purified by column chromatography on silica gel using a mixture of heptane/ethyl acetate (v/v 4:1 to 1:1) as eluent. The title compound was obtained as a brown viscous oil (188 mg, 42%). MS ISP (m/e): 446.5 (50) [(M+H)$^+$], 337.4 (100)

b) [8-(3,4-Difluoro-phenyl)-[1,2,4]triazolo[1,5-a]pyridin-2-yl]-[(rac)-8-endo-3-(2-methyl-pyrimidin-4-yl)-3-aza-bicyclo[3.2.1]oct-8-yl]-amine To a solution of N-((rac)-8-endo-3-benzyl-3-azabicyclo[3.2.1]octan-8-yl)-8-(3,4-difluorophenyl)-[1,2,4]triazolo[1,5-a]pyridin-2-amine (70 mg, 157 µmol) in methanol (1.6 mL) was added one drop of 25% aqueous hydrogen chloride solution under an atmosphere of nitrogen and stirring. The reaction was hydrogenated over night at 1 bar. The catalyst was filtered off and washed with ethanol. The solvent was evaporated under reduced pressure. The residue was dissolved in ethanol (1.6 mL). Triethylamine (47.7 mg, 65.7 µL, 471 µmol) and 4-chloro-2-methylpyrimidine (25.0 mg, 189 µmol) were added and the reaction was heated to 150° C. for 30 minutes in a microwave oven. The solvent was removed under reduced pressure after cooling to room temperature and the residue was purified by column chromatography on silica gel using a gradient from ethyl acetate to ethyl acetate/methanol (v/v 9:1) as eluent. The title compound was obtained as a light yellow solid (36 mg, 51%).
MS ISP (m/e): 448.5 (100) [(M+H)$^+$], 225.0 (80).

EXAMPLE 31

[(rac)-8-(3,4-Difluoro-phenyl)-5,6,7,8-tetrahydro-[1,2,4]triazolo[1,5-a]pyridin-2-yl]-[(rac)-8-endo-3-(3-methyl-[1,2,4]thiadiazol-5-yl)-3-aza-bicyclo[3.2.1]oct-8-yl]-amine

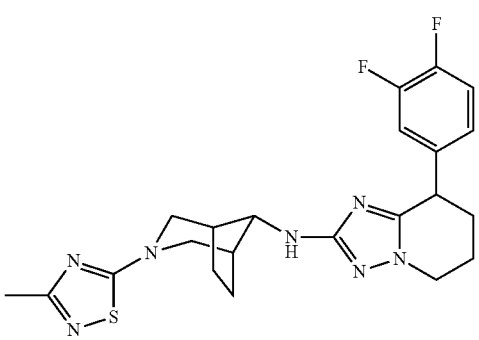 [SMILES: Cc1nsc(N2CC3CCC(C2)C3Nc2nc3n(n2)CCCC3c2ccc(F)c(F)c2)n1]

a) N-((rac)-8-endo-3-azabicyclo[3.2.1]octan-8-yl)-(rac)-(3,4-difluorophenyl)-5,6,7,8-tetrahydro-[1,2,4]triazolo[1,5-a]pyridin-2-amine hydrochloride A suspension of N-((rac)-8-endo-3-benzyl-3-azabicyclo[3.2.1]octan-8-yl)-(rac)-8-(3,4-difluorophenyl)-[1,2,4]triazolo[1,5-a]pyridin-2-amine (107 mg, 240 µmol), Pd/C 10% (107 mg, 1.01 mmol) and concentrated aqueous hydrochloric acid (90.0 mg, 75.0 µL, 617 µmol) in ethanol (6.27 mL) was hydrogenated for 24 hours at 50° C. under an atmosphere of hydrogen of 50 bar. The catalyst was filtered off and washed with ethanol and the solvent was removed under reduced pressure to yield the title compound as a white semisolid (85 mg, 89%). MS ISP (m/e): 360.6 (100) [(M+H)$^+$].

b) [(rac)-8-(3,4-Difluoro-phenyl)-5,6,7,8-tetrahydro-[1,2,4]triazolo[1,5-a]pyridin-2-yl]-[(rac)-8-endo-3-(3-methyl-[1,2,4]thiadiazol-5-yl)-3-aza-bicyclo[3.2.1]oct-8-yl]-amine To a solution of N-((rac)-8-endo-3-azabicyclo[3.2.1]octan-8-yl)-(rac)-(3,4-difluorophenyl)-5,6,7,8-tetrahydro-[1,2,4]triazolo[1,5-a]pyridin-2-amine hydrochloride (83 mg, 210 µmol) in ethanol (2.1 mL) was added triethylamine (63.6 mg, 87.7 µL, 629 µmol) and 5-chloro-3-methyl-1,2,4-thiadiazole (35.6 mg, 252 µmol) dissolved in ethanol (0.5 mL). The reaction was heated to 100° C. overnight. The solvent was removed under reduced pressure and the residue was purified by column chromatography on silica gel using a gradient from ethyl acetate to a mixture of ethyl acetate/methanol (v/v 9:1) as eluent. The title compound was obtained as a white solid (55 mg, 57%). MS ISP (m/e): 458.6 (100) [(M+H)$^+$], 230.0 (50).

The invention claimed is:
1. A compound of formula I

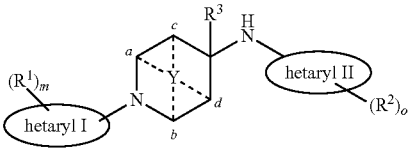

wherein
hetaryl I is a five or six membered heteroaryl group, containing 1 to 3 heteroatoms, selected from S and N;
hetaryl II is a six membered heteroaryl group, containing 1 to 3 heteroatoms, selected from S and N, or is a two membered ring system containing 1 to 4 heteroatoms selected from S and N, wherein at least one ring is aromatic in nature;
$R^1$ is lower alkyl, lower alkoxy, lower alkyl substituted by halogen or halogen;
$R^2$ is lower alkyl, lower alkyl substituted by halogen, halogen, lower alkoxy, cycloalkyl substituted by lower alkyl or lower alkyl substituted by halogen, lower alkyl substituted by hydroxy, furyl, O-benzyl, or $—(CH_2)_p$-phenyl which is optionally substituted by halogen, lower alkoxy, lower alkyl substituted by halogen, lower alkyl or cyano;
$R^3$ is hydrogen or lower alkyl;
Y is $—(CH_2)_2—$, which is bonded to ring carbon atoms c and d;
p is 0 or 1;
m is 0, 1 or 2; if m is 2 then each $R^1$ is the same or different; and
o is 0, 1 or 2, if o is 2, then each $R^2$ is the same or different;
or a pharmaceutically active acid addition salt thereof.
2. The compound of claim 1,

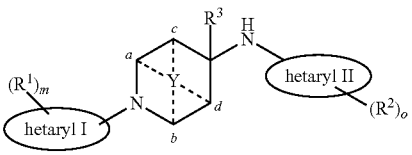

wherein
hetaryl I is pyridinyl, 1,2,4-thiadiazolyl, pyrazinyl or pyrimidinyl;
hetaryl II is [1,2,4]triazolo[1,5-a]pyridinyl, [1,2,4]triazolo[1,5-a]pyrazinyl, 5,6,7,8-tetrahydro-[1,2,4]triazolo[1,5-a]pyridinyl, [1,2,4]triazolo[1,5-c]pyrimidinyl, 4,5,6,7-tetrahydro-benzothiazolyl or pyrimidinyl;
$R^1$ is methyl, chloro or $CF_3$:
$R^2$ is methyl, n-propyl, fluoro, chloro, trifluoromethyl, methoxy, $—C(CH_3)_2OH$, O-benzyl, cyclohexyl substituted by methyl or trifluoromethyl, furyl, or $—(CH_2)_p$-phenyl which is optionally substituted by one, two or three halogen atoms selected from F and Cl, or by cyano or methoxy;
$R^3$ is hydrogen or methyl;
Y is $—(CH_2)_2—$ and is bonded to the two of the ring carbon atoms c and d;
p is 0 or 1;
m is 0, 1 or 2;
n is 2, or 3; and
o is 1 or 2, if o is 2, then each $R^2$ is the same or different;
or a pharmaceutically active acid addition salt thereof.
3. The compound of claim 1, wherein
hetaryl I is

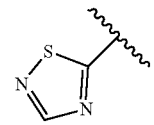 [SMILES: *c1ncns1]

and hetaryl II is a two membered ring system containing 1 to 4 heteroatoms.
4. The compound of claim 1, selected from the group consisting of
[(rac)-3-exo-8-(3-methyl-[1,2,4]thiadiazol-5-yl)-8-azabicyclo[3.2.1]oct-3-yl]-(4-phenyl-4,5,6,7-tetrahydrobenzothiazol-2-yl)-amine;
[(rac)-8-endo-3-(3-Methyl-[1,2,4]thiadiazol-5-yl)-3-azabicyclo[3.2.1]oct-8-yl]-[8-(2-chloro-4-fluoro-phenyl)-6-methyl-[1,2,4]triazolo[1,5-a]pyridin-2-yl]-amine;
[(rac)-8-endo-3-(3-Methyl-[1,2,4]thiadiazol-5-yl)-3-azabicyclo[3.2.1]oct-8-yl]-[8-(2-chloro-4-fluoro-phenyl)-6-fluoro-[1,2,4]triazolo[1,5-a]pyridin-2-yl]-amine;
[(rac)-8-endo-3-(3-Methyl-[1,2,4]thiadiazol-5-yl)-3-azabicyclo[3.2.1]oct-8-yl]-[8-(4-chloro-2-methoxy-phenyl)-[1,2,4]triazolo[1,5-a]pyridin-2-yl]-amine;
[(rac)-8-endo-3-(3-Methyl-[1,2,4]thiadiazol-5-yl)-3-azabicyclo[3.2.1]oct-8-yl]-[8-(3-cyano-4-fluoro-phenyl)-[1,2,4]triazolo[1,5-a]pyridin-2-yl]-amine;
[(rac)-8-endo-3-(3-methyl-[1,2,4]thiadiazol-5-yl)-3-azabicyclo[3.2.1]oct-8-yl]-[8-(3,4-difluoro-phenyl)-6-trifluoromethyl-[1,2,4]triazolo[1,5-a]pyridin-2-yl]-amine;
[(rac)-8-endo-3-(3-Methyl-[1,2,4]thiadiazol-5-yl)-3-azabicyclo[3.2.1]oct-8-yl]-[8-methoxy-[1,2,4]triazolo[1,5-a]pyridin-2-yl]-amine;
[(rac)-8-endo-3-(3-methyl-[1,2,4]thiadiazol-5-yl)-3-azabicyclo[3.2.1]oct-8-yl]-[8-chloro-6-trifluoromethyl-[1,2,4]triazolo[1,5-a]pyridin-2-yl]-amine;
[(rac)-8-endo-3-(3-Methyl-[1,2,4]thiadiazol-5-yl)-3-azabicyclo[3.2.1]oct-8-yl]-[5,6-dimethyl-[1,2,4]triazolo[1,5-a]pyridin-2-yl]-amine; and
[(rac)-8-endo-3-(3-Methyl-[1,2,4]thiadiazol-5-yl)-3-azabicyclo[3.2.1]oct-8-yl]-[8-benzyloxy-[1,2,4]triazolo[1,5-a]pyridin-2-yl]-amine
or a pharmaceutically active acid addition salt thereof.
5. The compound of claim 1, selected from the group consisting of
[(rac)-8-endo-3-(3-Methyl-[1,2,4]thiadiazol-5-yl)-3-azabicyclo[3.2.1]oct-8-yl]-[5-propyl-[1,2,4]triazolo[1,5-a]pyridin-2-yl]-amine;
[(rac)-8-endo-3-(3-Methyl-[1,2,4]thiadiazol-5-yl)-3-azabicyclo[3.2.1]oct-8-yl]-(5-phenyl-[1,2,4]triazolo[1,5-a]pyrazin-2-yl)-amine;
[(rac)-8-endo-3-(3-Methyl-[1,2,4]thiadiazol-5-yl)-3-azabicyclo[3.2.1]oct-8-yl]-[5-trifluoromethyl-[1,2,4]triazolo[1,5-a]pyridin-2-yl]-amine;
[(rac)-8-endo-3-(3-methyl-[1,2,4]thiadiazol-5-yl)-3-azabicyclo[3.2.1]oct-8-yl]-[6-chloro-8-(3,4-difluoro-phenyl)-[1,2,4]triazolo[1,5-a]pyridin-2-yl]-amine;
[(rac)-8-endo-3-(3-methyl-[1,2,4]thiadiazol-5-yl)-3-azabicyclo[3.2.1]oct-8-yl]-[7-methyl-5-propyl-[1,2,4]triazolo[1,5-c]pyrimidin-2-yl]-amine;

[(rac)-8-endo-3-(3-methyl-[1,2,4]thiadiazol-5-yl)-3-aza-bicyclo[3.2.1]oct-8-yl]-[8-(4,4-dimethyl-cyclohexyl)-[1,2,4]triazolo[1,5-a]pyridin-2-yl]-amine;

[(rac)-8-endo-3-(3-methyl-[1,2,4]thiadiazol-5-yl)-3-aza-bicyclo[3.2.1]oct-8-yl]-(7-furan-2-yl-[1,2,4]triazolo[1,5-a]pyrimidin-2-yl)-amine;

[(rac)-8-endo-3-(3-Methyl-[1,2,4]thiadiazol-5-yl)-3-aza-bicyclo[3.2.1]oct-8-yl]-[7-trifluoromethyl-[1,2,4]triazolo[1,5-a]pyridin-2-yl]-amine;

[(rac)-8-endo-3-(3-Methyl-[1,2,4]thiadiazol-5-yl)-3-aza-bicyclo[3.2.1]oct-8-yl]-[8-(4-trifluoromethyl-cyclohexyl)-[1,2,4]triazolo[1,5-a]pyridin-2-yl]-amine;

[(rac)-8-(4-Fluoro-phenyl)-5,6,7,8-tetrahydro-[1,2,4]triazolo[1,5-a]pyridin-2-yl]-[(rac)-8-exo-3-(3-methyl-[1,2,4]thiadiazol-5-yl)-3-aza-bicyclo[3.2.1]oct-8-yl]-amine; and

[(rac)-8-(3,4-Difluoro-phenyl)-5,6,7,8-tetrahydro-[1,2,4]triazolo[1,5-a]pyridin-2-yl]-[(rac)-8-endo-3-(3-methyl-[1,2,4]thiadiazol-5-yl)-3-aza-bicyclo[3.2.1]oct-8-yl]-amine or a pharmaceutically active acid addition salt thereof.

6. The compound of claim 1, wherein
hetaryl I is

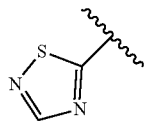 [SMILES: *c1ncns1]

and hetaryl II is a six membered heteroaryl group, containing 1 to 3 heteroatoms, selected from S and N.

7. The compound of claim 1, wherein the compound is 2-{6-(4-chloro-benzyl)-2-[(rac)-3-endo-8-(3-methyl-[1,2,4]thiadiazol-5-yl)-8-aza-bicyclo[3.2.1]-oct-3-ylamino]-pyrimidin-4-yl}-propan-2-ol.

8. The compound of claim 1, wherein hetaryl I is

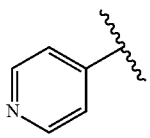

and hetaryl II is a two membered ring system containing 1 to 4 heteroatoms.

9. The compound of claim 1, selected from the group consisting of

[(rac)-3-exo-8-(2-chloropyridin-4-yl)-8-aza-bicyclo[3.2.1]oct-3-yl]-[8-(3,4-difluorophenyl)-6-methyl-[1,2,4]triazolo[1,5-a]pyridin-2-yl]-amine and

[8-(3,4-difluoro-phenyl)-[1,2,4]triazolo[1,5-a]pyridin-2-yl]-[(rac)-8-endo-3-(2-trifluoromethyl-pyridin-4-yl)-3-aza-bicyclo[3.2.1]oct-8-yl]-amine.

10. The compound of claim 1, wherein heteroaryl I is

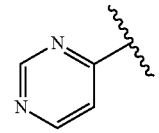

and hetaryl II is a two membered ring system containing 1 to 4 heteroatoms.

11. The compound of claim 1, selected from the group consisting of

[(rac)-8-endo-3-(6-methyl-pyrimidin-4-yl)-3-aza-bicyclo[3.2.1]oct-8-yl]-[8-(2,3,4-trifluoro-phenyl)-[1,2,4]triazolo[1,5-a]pyridin-2-yl]-amine;

[(rac)-8-endo-3-(6-Methyl-pyrimidin-4-yl)-6-oxa-3-aza-bicyclo[3.2.1]oct-8-yl]-[8-(2,3,4-trifluoro-phenyl)-[1,2,4]triazolo[1,5-a]pyridin-2-yl]-amine;

[(rac)-8-exo-Methyl-3-(6-methyl-pyrimidin-4-yl)-3-aza-bicyclo[3.2.1]oct-8-endo-yl]-[8-(2,3,4-trifluoro-phenyl)-[1,2,4]triazolo[1,5-a]pyridin-2-yl]-amine; and

[8-(3,4-Difluoro-phenyl)-[1,2,4]triazolo[1,5-a]pyridin-2-yl]-[(rac)-8-endo-3-(2-methyl-pyrimidin-4-yl)-3-aza-bicyclo[3.2.1]oct-8-yl]-amine or a pharmaceutically active acid addition salt thereof.

12. The compound of claim 1, wherein said compound is 3-(6-methyl-pyrimidin-4-yl)-3-aza-bicyclo[3.2.1]oct-8-yl-[8-(2,3,4-trifluoro-phenyl)-[1,2,4]triazolo[1,5-a]pyridin-2-yl]-amine or a pharmaceutically active acid addition salt thereof.

13. A pharmaceutical composition comprising a therapeutically effective amount of a compound of formula I

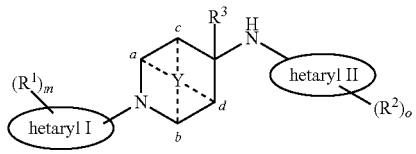

wherein
hetaryl I is pyridinyl, pyrazinyl or pyrimidinyl;
hetaryl II is [1,2,4]triazolo[1,5-a]pyridinyl, [1,2,4]triazolo[1,5-a]pyrazinyl, 5,6,7,8-tetrahydro-[1,2,4]triazolo[1,5-a]pyridinyl, [1,2,4]triazolo[1,5-c]pyrimidinyl, 4,5,6,7-tetrahydro-benzothiazolyl or pyrimidinyl;
$R^1$ is methyl, chloro or $CF_3$:
$R^2$ is methyl, n-propyl, fluoro, chloro, trifluoromethyl, methoxy, —C(CH$_3$)$_2$OH, O-benzyl, cyclohexyl substituted by methyl or trifluoromethyl, furyl, or —(CH$_2$)$_p$-phenyl which is optionally substituted by one, two or three halogen atoms selected from F and Cl, or by cyano or methoxy;
$R^3$ is hydrogen or methyl;
Y is —(CH$_2$)$_2$—, which is bonded to ring carbon atoms c and d;
p is 0 or 1;
m is 0, 1 or 2;
and
o is 1 or 2, if o is 2, then each $R^2$ is the same or different;
or a pharmaceutically active acid addition salt thereof
and a pharmaceutically acceptable carrier.

* * * * *